(12) United States Patent
Jones et al.

(10) Patent No.: US 7,723,055 B2
(45) Date of Patent: May 25, 2010

(54) DIAGNOSING AND TREATING HEMATOPOIETIC CANCERS

(75) Inventors: Stephen N. Jones, Shrewsbury, MA (US); Huiling Liang, North Grafton, MA (US); German Pihan, Weston, MA (US)

(73) Assignee: University of Massachusetts, Boston, MA (US)

(*) Notice: Subject to any disclaimer, the term of this patent is extended or adjusted under 35 U.S.C. 154(b) by 0 days.

(21) Appl. No.: 11/874,703

(22) Filed: Oct. 18, 2007

(65) Prior Publication Data

US 2008/0090245 A1 Apr. 17, 2008

Related U.S. Application Data

(62) Division of application No. 10/719,054, filed on Nov. 20, 2003, now abandoned.

(60) Provisional application No. 60/428,549, filed on Nov. 21, 2002.

(51) Int. Cl.
*G01N 33/53* (2006.01)
*C12Q 1/00* (2006.01)

(52) U.S. Cl. .............................. 435/7.23; 435/7.2; 435/4

(58) Field of Classification Search ................ 435/7.23, 435/7.2, 4
See application file for complete search history.

(56) References Cited

U.S. PATENT DOCUMENTS

| | | | |
|---|---|---|---|
| 4,215,051 A | 7/1980 | Schroeder et al. | |
| 4,522,811 A | 6/1985 | Eppstein et al. | |
| 4,683,202 A | 7/1987 | Mullis | |
| 4,868,103 A | 9/1989 | Stavrianopoulos et al. | |
| 5,223,409 A | 6/1993 | Ladner et al. | |
| 5,272,071 A | 12/1993 | Chappel | |
| 5,283,317 A | 2/1994 | Saifer et al. | |
| 5,328,470 A | 7/1994 | Nabel et al. | |
| 5,459,039 A | 10/1995 | Modrich et al. | |
| 5,498,531 A | 3/1996 | Jarrell | |
| 5,631,169 A | 5/1997 | Lakowicz et al. | |
| 5,695,937 A | 12/1997 | Kinzler et al. | |
| 5,851,984 A | 12/1998 | Matthews et al. | |
| 5,854,033 A | 12/1998 | Lizardi | |
| 5,876,742 A | 3/1999 | Cochrum et al. | |
| 6,159,462 A | 12/2000 | Matthews et al. | |
| 2002/0049177 A1 | 4/2002 | Clark et al. | |

FOREIGN PATENT DOCUMENTS

WO WO 91/06667 5/1991
WO WO 94/10300 5/2004

OTHER PUBLICATIONS

Shaughnesy et al (Immunological Reviews, 194: 140-163, 2003.*
Cheung et al (Nature Genetics, 33: 422-425, 2003.*
Wulfkuhle et al, (European Journal of Cancer, 40: 2623-2632, 2004.*
Iozzo et al, (Cancer Research, 55: 3495-3499, 1995.*
Austin et al., "A role for the Wnt gene family in hematopoiesis: expansion of multilineage progenitor cells," Blood 89(10):3624-635 (1997).
Bai et al., Effective transduction and stable transgene expression in human blood cells by a third-generation lentiviral vector, Gene Ther. 10(17):1446-57 (2003).
Becker, "The current status of gene therapy in autologous transplantation," Acta. Haematol., 114(4):188-197, (2005).
Brandon et al., "WNT signaling modulates the diversification of hematopoietic cells." Blood 96(13) 4132-4141 (2000).
Budak-Alpdogan et al., "Hematopoietic stem gene therapy with drug resistance genes: an update," Cancer Gene Ther., 12(11):849-863, (2005).
Cavazzana-Calvo et al., "Gene therapy of human severe combined immunodeficiency (SCID)-X1 disease," Science 288(5466):669-72 (2000).
Fry and Mackall, "Interleukin-7: from bench to clinic," Blood 99(11):3892-904 (2002).
Gage, "Cell Therapy," Nature, 392(6679 Suppl):18-24, (1998).
He et al., "A member of the frizzled protein family mediating axis induction by Wnt-5a," Science 275:652-654 (1997).
Holmen et al., "A novel set of Wnt-Frizzled fusion proteins identifies receptor components that activate beta-catenin-dependent signaling," J. Biol. Chem. 277(38):34727-35 (2002).
Iozzo et al., "Aberrant expression of the growth factor Wnt-5A in human malignancy," Cancer Res. 55(16):3495-499 (1995).
Jönsson et al., "Loss of Wnt-5a protein is associated with early relapse in invasive ductal breast carcinomas," Cancer Res. 62(2):409-16 (2002).
Jordan et al., "Long-term repopulating abilities of enriched fetal liver stem cells measured by competitive repopulation," Exp. Hematol. 23:1011-1015 (1995).
Jurecic et al., "Enrichment and functional characterization of Sca-1$^+$WGA$^+$, Lin-WGA$^+$, Lin-Sca-1$^+$, and Lin-Sca-1$^+$WGA$^+$bone marrow cells from mice with an Ly-6a haplotype," Blood 82(9):2673-83 (1993).
Kawakami et al., "WNT signals control FGF-dependent limb initiation and AER induction in the chick embryo," Cell 104(6):891-900 (2001).
Kohn et al, "Gene therapy for genetic Haematological disorders and immunodeficiencies," J. Intern. Med., 249(4):379-390, (2001).
Kühl et al., "Ca$^{2+}$/calmodulin-dependent protein kinase II is stimulated by Wnt and Frizzled homologs and promotes ventral cell fates in Xenopus," J. Biol. Chem. 275(17):12701-11 (2000).
Kühl et al., "Antagonistic regulation of convergent extension movements in Xenopus by Wnt/beta-catenin and Wnt/Ca2$^+$signaling," Mech Dev. 106(1-2):61-76 (2001).
Lejeune et al., "Wnt5a cloning, expression, and up-regulation in human primary breast cancers," Clin. Cancer Res 1(2):215-22 (1995).

(Continued)

*Primary Examiner*—Anne-Marie Falk
*Assistant Examiner*—Magdalene K Sgagias
(74) *Attorney, Agent, or Firm*—Fish & Richardson P.C.

(57) ABSTRACT

Described herein are methods and compositions comprising Wnt5a for the diagnosis and treatment of hematopoietic cancers, and methods of identifying therapeutic compounds for the treatment of hematopoietic cancers.

10 Claims, 11 Drawing Sheets

OTHER PUBLICATIONS

Li and Johnson, "Murine hematopoietic stem and progenitor cells: I. Enrichment and biologic characterization," Blood 85(6):1472-9 (1995).

Liang et al., "Wnt5a inhibits B cell proliferation and functions as a tumor suppressor in hematopoietic tissue," Cancer Cell 4(5):349-60 (2003).

Liang et al., "A role for Wnt5a in B cell growth and tumorigenesis," Proc. Amer. Assoc. Cancer Research, Annual Meeting 43:667, Abstract #3310 (2002).

Olson et al., "Reversion of uroepithelial cell tumorigenesis by the ectopic expression of human wnt-5a," Cell Growth Differ. 8(4):417-23 (1997).

Phillips et al., "The genetic program of hematopoietic stem cells," Science 288(5471):1635-40 (2000).

Rimerman et al., "Wnt1 and MEK1 cooperate to promote cyclin D1 accumulation and cellular transformation," J. Biol. Chem. 275(19):14736-42 (2000).

Scanlon, "Cancer Gene Therapy: Challenges and Opportunities," Anticancer Research, 24:3-7 (2004).

Schmidt-Wolf and Schmidt-Wolf, "Gene therapy for hematological malignancies," Clin. Exp. Med. 3(1):4-14 (2003).

Slusarski et al., "Modulation of embryonic intracellular $Ca^{2+}$ signaling by Wnt-5A," Dev. Biol. 182(1):114-20 (1997).

Sorrentino, "Clinical Strategies for Expansion of Haematopoietic Stem Cells," Nature, 4:878-888, (2004).

Szilvassy et al., "Homing and engraftment defects in ex vivo expanded murine hematopoietic cells are associated with downregulation of beta1 integrin," Exp. Hematology, 29:1494-1502, (2001).

Toyofuku et al., "Wnt/frizzled-2 signaling induces aggregation and adhesion among cardiac myocytes by increased cadherin-beta-catenin complex," J. Cell. Biol. 150(1):225-41 (2000).

Van Den Berg et al., "Role of members of the Wnt gene family in human hematopoiesis," Blood 92(9):3189-202 (1998).

Weeraratna et al., "Wnt5a signaling directly affects cell motility and invasion of metastatic melanoma," Cancer Cell. 1 (3):279-88 (2002).

Whitlock et al., "Murine B cell lymphopoiesis in long term culture," J. Immunol. Methods 67(2):353-69 (1984).

Willert et al., "A transcriptional response to Wnt protein in human embryonic carcinoma cells," BMC Dev. Biol. 2(1):8. Epub Jul. 2, 2002.

Yamaguchi et al., "A Wnt5a pathway underlies outgrowth of multiple structures in the vertebrate embryo," Development 126(6):1211-23 (1999).

Gilliland et al., "Focus on acute leukemias," Cancer Cell, 1:417-420 (2002).

Khan et al., "Activation of Wnt/β-catenin pathway mediates growth and survival in B-cell progenitor acute lymphoblastic leukaemia," British Journal of Haematology, 138:338-348 (2007).

Liang et al., "Noncanonical Wnt signaling promotes apoptosis in thymocyte development," Journal of Experimental Medicine, 204(13):3077-3084 (2007).

Martin et al., "Methylation status of Wnt signaling of pathway genes affects the clinical outcome of Philadelphia-positive acute lymphoblastic leukemia," Cancer Science, 99(9):1865-1868 (2008).

Nemeth et al., "Wnt5a inhibits canonical Wnt signaling in hematopoietic stem cells and enhances repopulation," Proceedings of the National Academy of Sciences, 104(39):15436-15441 (2007).

Roman-Gomez et al., "WNT5A, a putative tumour suppressor of lymphoid malignancies, is inactivated by aberrant methylation in acute lymphoblastic leukaemia," European Journal of Cancer, 43:2736-2746 (2007).

Stanley, J., "Chapter 26: Tumor Immunology," In: *Essential of Immunology and Serology*, Delmar:New York, pp. 438-450 (2002).

Van Ettan et al., "Focus on myeloproliferative diseases and myelodysplastic syndromes," Cancer Cell, 6:547-552 (2004).

Ying et al., "WNT5A is epigenetically silenced in hematologic malignancies and inhibits leukemia cell growth as a cell suppressor," Blood, 110(12):4130-4132 (2007).

Zhan et al., "Global gene expression profiling of multiple myeloma, monoclonal gammopathy of undetermined significance, and normal bone marrow plasma cells," Blood, 99:1745-1757 (2002).

* cited by examiner

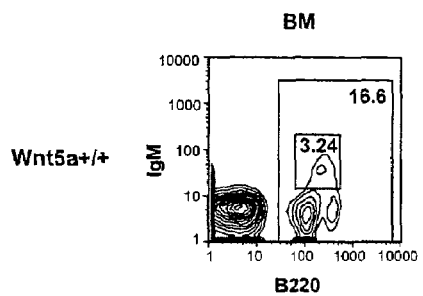
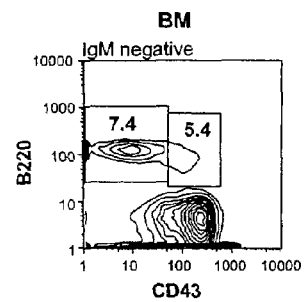
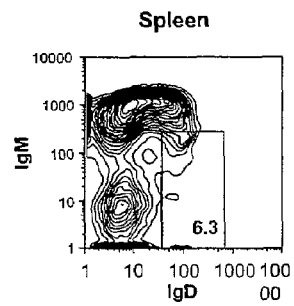
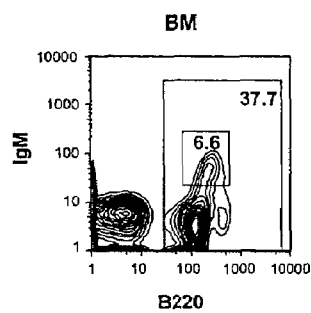
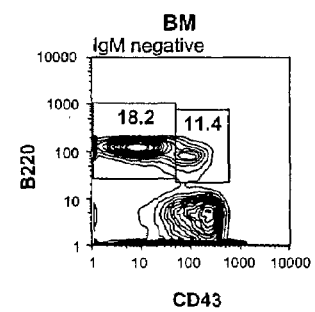
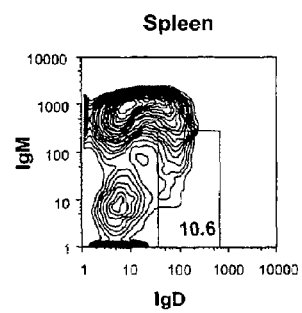
FIG. 17A  FIG. 17B  FIG. 17C
FIG. 17D  FIG. 17E  FIG. 17F
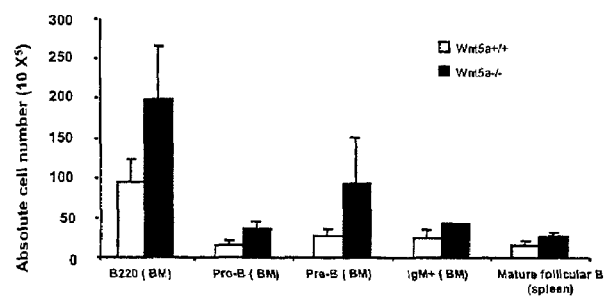
FIG. 18

US 7,723,055 B2

DIAGNOSING AND TREATING HEMATOPOIETIC CANCERS

CLAIM OF PRIORITY

This application is a divisional of U.S. patent application Ser. No. 10/719,054, filed on Nov. 20, 2003, now abandoned and claims the benefit of U.S. Provisional Patent Application Ser. No. 60/428,549, filed on Nov. 21, 2002. The entire contents of both applications are incorporated herein by reference.

TECHNICAL FIELD

This invention relates to cancer therapeutics, diagnostics, and methods of screening for chemotherapeutic agents.

BACKGROUND

Wnt5a (wingless-related MMTV integration site 5a) is a member of a large family of cysteine-rich growth factors. Proteins in this family are highly conserved and naturally secreted; upon secretion, they provide signals that regulate cell-cell interactions during embryogenesis. More specifically, the Wnt proteins seem to be critical for pattern formation, cell fate determination, and other events required for proper embryonic development. Researchers have studied the mechanisms by which Wnt proteins function in several different ways. They have, for example, performed genetic studies in Drosophila and Caenorhabditis elegans and biochemical assays in cell culture. They have also altered gene expression in Xenopus embryos and found that mutated Wnt-encoding genes in the mouse lead to specific developmental defects.

On a cellular level, Wnt5a binds to members of the Frizzled (Fzd) family of seven-transmembrane domain receptors on the cell surface, and this triggers a series of intracellular events that ultimately regulate gene transcription. These intracellular events are grouped according to two known signaling pathways, the canonical Wnt/β-catenin pathway (He et al., Science 275:652-654, 1997; Toyofuku et al., J. Cell Biol. 150:225-41, 2000; Kawakami et al., Cell 104:891-900, 2001) and the Wnt/$Ca^{++}$ pathway (Slusarski et al., Dev. Biol. 182:114-120, 1997; Kuhl et al., J. Biol. Chem. 275:12701-12711, 2000; and Kuhl et al., Mech. Dev. 106:61-76, 2001) (FIG. 1). Wnt5a-mediated release of intracellular $Ca^{++}$ leads to the phosphorylation of both protein kinase C (PKC) and calcium/calmodulin dependent protein kinase II (CamK II), and the activation of these two kinases blocks the Wnt/β-catenin signaling cascade via phosphorylation of dishevelled (dvl) (by PKC) or Lymphoid Enhancer-binding Factor (LEF-1) (by CamK II). These distinct Wnt signaling cascades control convergent extension movements in Xenopus, and Wnt5a has been shown to regulate the expression of β-catenin responsive genes in this system (Kuhl et al., Mech. Dev. 106:61-76, 2001). The signaling pathway that is induced may be governed by the cell surface Fzd receptor to which Wnt5a binds (Holmen et al., J. Biol. Chem. (in press), 2002).

Wnt genes and Wnt signaling have been studied in the context of cellular proliferation, but the role of Wnt5a in tumor development is still unclear. Unlike members of the Wnt1 class of transforming Wnt genes, transfection with Wnt5a fails to transform C57MG cells, an epithelial cell line derived from normal mouse mammary tissue (Willert et al., BMC Dev. Biol. 2:8, 2002), and ectopic expression of human Wnt5a in a transformed uroepithelial cell line inhibited growth (Olson et al., Cell Growth Differ. 8:417-23, 1997). However, addition of Wnt5a to the media of cultured cells has also been reported to stimulate hematopoietic stem cell proliferation including lymphoid and myeloid progenitors (Van Den Berg, et al., Blood 92:3189-202, 1998; Austin, et al., Blood 89:3624-3635, 1997). Upregulation of WNT5a has been observed in various human cancers (Lejeune et al., Clin. Cancer Res. 1:215-222, 1995; Tozzo et al., Cancer Res. 55:3495-3499, 1995) and WNT5a has recently been reported to facilitate cell invasion in human metastatic melanoma (Weeraratna et al., Cancer Cell 1:279-88, 2002).

SUMMARY OF THE INVENTION

The compositions and methods described herein are based, in part, on evidence that Wnt5a plays a role in B cell proliferation and differentiation, and acts as a suppressor of B cell proliferation to suppress hematopoietic malignancies.

Accordingly, described herein are compositions (e.g., pharmaceutically acceptable compositions) that contain Wnt5a, sequences encoding it, or biologically active mutants thereof, therapeutic, diagnostic, and screening methods that utilize Wnt5a; and substances or agents identified by the screening methods. Generally, the methods involve (but are not limited to) detecting or modulating the level of Wnt5a expression or activity, or identifying compounds that modulate that expression or activity. As described further herein, an activity that can be assessed can be one that is immediately dependent upon Wnt5a (e.g., receptor binding) or an activity that occurs "downstream" of a Wnt5a-dependent event (e.g., an increase intracellular calcium, phosphorylation of PKC and/or CAMK II, or expression of c-myc and/or cyclin D1). These activities may be, but are not necessarily, reflected by changes in gene transcription.

In one aspect, the methods described herein include a method of determining whether a subject (e.g., a human patient) has, or is at risk of developing, a hematopoietic cancer associated with a reduction in wingless-related MMTV integration site 5a (Wnt5a) gene expression or activity or protein activity. The method includes providing a biological sample comprising a test cell from the subject; and determining the level of Wnt5a gene expression or activity or protein activity within the test cell. A reduction in the level of Wnt5a gene expression or activity or protein activity in the test cell, relative to that in a control cell, indicates that the subject has, or is at risk of developing, a hematopoietic cancer. The method can also optionally include communicating the level of Wnt5a expression to a physician or other health care provider.

The test cell can be, for example, a somatic cell, e.g., a type of cell that becomes malignant in the event of a hematopoietic cancer, e.g., a blood cell such as a B cell, a T cell, an eosinophil, basophil, erythrocyte, neutrophil, granulocyte, or monocyte. The control cell can be, for example, a somatic cell, e.g., a type of cell that becomes malignant in the event of a hematopoietic cancer, e.g., a blood cell such as a B cell, a T cell, an eosinophil, basophil, erythrocyte, neutrophil, granulocyte, or monocyte. Typically, the control cell and the test cell will be the same type of cell.

The methods can include culturing one or both of the test cell and the control cell before determining the level of expression or activity of Wnt5a.

The level of Wnt5a gene expression or activity or protein expression or activity can be determined by exposing mRNA isolated from the test cell to a Wnt5a-specific nucleic acid primer or probe; or exposing protein isolated from the test cell to a Wnt5a-specific antibody. Alternatively or additionally, Wnt5a gene expression or activity or protein expression or activity can be determined by assessing the level of expression of cyclin D1 and/or by assessing the extent of phosphorylation of protein kinase C (PKC), calmodulin kinase II (CamK II), dishevelled (dvl), or LEF-1.

The new methods also include methods of identifying an anti-hematopoietic cancer agent. The methods include exposing a sample comprising a Wnt5a-expressing cell to a test agent; and determining the level of Wnt5a expression or activity in the Wnt5a-expressing cell. An increase in Wnt5a expression or activity, relative to the level of Wnt5a expression or activity in a control cell, indicates that the test agent is an anti-cancer agent. One or both of the Wnt5a-expressing cell and the control cell can be a human cell, and/or a blood cell, e.g., a lymphoid cell or a myeloid cell (for example, a B cell, a T cell, an eosinophil, a basophil, an erythrocyte, a neutrophil, a granulocyte, or a monocyte). One or both of the Wnt5a-expressing cell and the control cell can be cultured before determining the level of expression or activity of Wnt5a The test agent can include, for example, a polypeptide, a nucleic acid molecule, a small non-peptide, non-oligonucleotide molecule, or a chemical entity.

The new methods also include methods of treating a subject (e.g., a human patient) who has, or who is at risk of developing, a hematopoietic cancer associated with a reduction in Wnt5a, the method comprising administering to the subject a nucleic acid molecule comprising a sequence that encodes Wnt5a or a biologically active fragment or mutant thereof, and, optionally, a sequence that encodes a detectable marker, wherein the amount of the nucleic acid molecule delivered is sufficient to generate a therapeutically effective amount of Wnt5a. The nucleic acid molecule, which can include an expression vector, can be delivered to the subject in connection with a liposome or liposomal complex. The administering can be accomplished by removing a cell from the subject; transducing the cell with a nucleic acid molecule comprising a sequence that encodes Wnt5a or a biologically active fragment or mutant thereof, and, optionally, a sequence that encodes a detectable marker; optionally culturing the cell (either before or after transducing the cell with the Wnt5a nucleic acid; and returning the cell to the subject.

Hematopoietic cancers associated with a reduction in Wnt5a gene expression or activity or protein expression or activity can include, but is not limited to, leukemia (e.g., chronic leukemia or acute leukemia, e.g., acute myeloid leukemia or acute lymphoblastic leukemia), lymphoma (e.g., Hodgkin's and non-Hodgkin's Lymphoma, e.g., B cell lymphoma, Burkitt's lymphoma, diffuse cell lymphoma, follicular lymphoma, immunoblastic large cell lymphoma, lymphoblastic lymphoma, mantle cell lymphoma, mycosis fungoides, post-transplantation lymphoproliferative disorder, small non-cleaved cell lymphoma, and T-cell lymphoma), and myeloma.

The methods can be practiced by, for example, determining whether the level of Wnt5a, e.g., Wnt5a expression or activity, is altered (e.g., decreased) in a biological sample (e.g., a blood cell, a homogeneous or heterogeneous group of blood cells, or a hematopoietic tissue that is within or obtained from a subject, e.g., a human or veterinary patient or experimental animal). As Wnt5a can function as a tumor suppressor, a cell (e.g., a B cell) containing a decreased level of Wnt5a (or a normal amount of dysfunctional Wnt5a, i.e., Wnt5a that cannot signal through the non-canonical Wnt/$Ca^{++}$ pathway) is likely to be more prone to loss of cell cycle control, which may or may not have occurred at the time the level of Wnt5a is detected. Thus, subjects who carry cells (e.g., B cells) with reduced levels of Wnt5a have an increased chance of developing a hematopoietic malignancy (i.e., those subjects may be determined to have a higher than expected risk of hematopoietic malignancy).

The subject can be any animal (e.g., a mammal such as a human) that normally expresses Wnt5a; it is expected that the methods will be carried out more commonly in connection with human subjects, but the subject can also be another primate (e.g., a monkey or chimpanzee), a domesticated animal (e.g., a dog or cat), livestock (such as a horse, cow, pig, sheep, or goat), or an animal commonly used in laboratory studies (e.g., a mouse, rat, hamster, gerbil, or guinea pig). The new methods can also be carried out with respect to other animals (e.g., avians, such as chickens or other birds, and amphibians, such as frogs, toads, and newts). When non-human subjects or non-human cells are used, probes that recognize Wnt5a within those subjects or cells (e.g., murine Wnt5a) can be used. Moreover, while the methods described herein can be carried out on unaltered cells, they may also be carried out with cells that have been altered (e.g., cells that overexpress Wnt5a or another tumor suppressor gene; cells that have been treated with a chemotherapeutic agent or other test compound; or cells that express a detectable marker).

In one aspect, the new methods can be used to screen test agents and identify those useful in treating or preventing (including reducing the risk of) cancer. These methods can be carried out by exposing a cell, such as a Wnt5a-expressing blood cell (e.g., a hematopoietic stem cell, a lymphoid cell, such as a B cell or a T cell, or a myeloid cell, such as an eosinophil, basophil, erythrocyte, neutrophil, granulocyte, or monocyte) to a test agent and determining whether the test agent alters the expression or activity of Wnt5a within the cell. The cell can be in vivo or in cell culture (e.g., a hematopoietic tissue explant or cell line), and an increase in Wnt5a expression or activity in the blood cell can indicate that the agent is (or is a candidate for development as) a chemotherapeutic or an agent that, when administered to a subject, reduces the subject's risk of developing a hematopoietic cancer. Conversely, an agent that decreases the expression or activity of Wnt5a in the cell is (or merits further testing as) a candidate hematologic carcinogen or agent that, when administered to a subject, increases the subject's risk of developing a hematopoietic cancer.

In some embodiments, the methods can include administering a test agent to an animal, e.g., an experimental animal, e.g., an experimental animal that has reduced Wnt5a expression in its blood cells (e.g., B cells), and determining whether the test agent (a) affects a parameter associated with a hematopoietic malignancy in the animal, e.g., the occurrence, onset, development, severity, lethality, or duration of a hematopoietic malignancy, and/or (b) affects a parameter associated with non-hematopoietic malignancy in the animal, e.g., the occurrence, onset, development, severity, lethality, or duration of a non-hematopoietic malignancy, e.g., a cancer of the breast, lung, gastrointestinal tract, genitourinary tract, or skin.

In some embodiments, the methods can further include selecting a test agent that positively affects a parameter associated with a hematopoietic malignancy, and positively affects or does not affect a parameter associated with a non-hematopoietic malignancy, and further evaluating the therapeutic efficacy of the selected test agent. In some embodiments, the test agent is a potential therapeutic agent for the treatment of a hematopoietic malignancy, and the method includes evaluating the test agent for an effect on non-hematopoietic malignancy, e.g., non-hematologic carcinogenicity.

Conversely, in some embodiments, the method can further include selecting a test agent that positively affects or does not affect a parameter associated with a hematopoietic malignancy, and positively affects a parameter associated with a non-hematopoietic malignancy, and further evaluating the therapeutic efficacy of the selected test agent. In some embodiments, the test agent is a potential therapeutic agent for the treatment of a non-hematopoietic malignancy, and the method includes evaluating the test agent for an effect on hematopoietic malignancy, e.g., hematologic carcinogenicity.

The test agent can be virtually any substance, including naturally occurring, modified, or synthetic polypeptides, including antibodies, antibody fragments, single chain antibodies, peptidomimetics, or peptoids; naturally occurring or synthetic nucleic acid molecules; small, non-peptide molecules (<30 kDa), or chemical entities). The level of expression or activity can be assessed relative to that in a control cell or tissue (e.g., an identical or comparable cell that has not been exposed to the test agent).

The expression or activity of Wnt5a can be assessed in conjunction with other parameters. For example, one can expose a blood cell (e.g., a B cell) to a test agent and a known hematologic carcinogen (e.g., a carcinogen known to cause a hematopoietic malignancy, or to increase the subject's risk of developing a hematopoietic malignancy) and assess the ability of the test agent to alter Wnt5a expression or activity and to alter the expected response to the carcinogen (e.g., loss of cell cycle control and/or cell proliferation). A test agent that inhibits, for example, loss of cell cycle control, is (or may be developed as) a chemotherapeutic agent or an agent that decreases a subject's risk of developing cancer.

In addition to, or as an alternative to, assessing Wnt5a expression or activity, one can assess the ability of a test agent (alone or in the presence of a carcinogen) to alter a Wnt5a-dependent function (e.g., an activity that occurs downstream of Wnt5a receptor activation). For example, one can assess cyclin D1 mRNA expression or other Wnt5a-activated gene transcription. Wnt5a activity can also be determined by assessing Wnt5a-dependent phosphorylation of protein kinase C (PKC), or calcium/calmodulin dependent protein kinase II (CamK II), disheveled (dvl)(phosphorylated by PKC); and/or LEF-1 (phosphorylated by CamK II). These methods can be carried out using any cell that expresses or is made to express a Wnt5a receptor, e.g., any blood cell such as a B cell, including a cell from any of the subjects listed above, and the level of expression or activity can be compared to that in an appropriate control cell. The length of time the cells (test cells and control cells) are exposed to the test agent can vary substantially, so long as it is sufficient to permit modulation of Wnt5a or a Wnt5a-dependent function to occur.

The invention also features methods of treating a subject who has, or who is at risk of developing, a hematopoietic cancer. These methods can be carried out, for example, by administering to the subject, or to a cell from the subject (e.g., a blood cell that was removed from, and is to be returned to, the subject), a nucleic acid molecule that encodes Wnt5a or a biologically active fragment or other mutant thereof. The nucleic acid molecule, compositions (e.g., pharmaceutically acceptable compositions) that contain it (including those in which the nucleic acid is administered by way of liposomes or liposomal complexes), and routes of administration are discussed further herein. A therapeutically effective amount will be sufficient to reduce the subject's risk of a hematopoietic cancer or to suppress the growth (e.g., proliferation of) malignant blood cells, e.g., B cells. Alternatively, one can administer Wnt5a polypeptides per se or biologically active (i.e., tumor suppressing) fragments or other mutants thereof, an agent that increases the expression or activity of Wnt5a; or an agent that increases the expression or activity of a Wnt5a-activated molecule (e.g., a molecule that lies downstream in the Wnt5a effector pathway; these molecules can carry out Wnt5a-dependent functions).

Also described are kits containing one or more of the components required to carry out the methods described above. For example, the invention features kits that include Wnt5a probes (e.g., a nucleic acid, an antibody, or an antigen-binding fragment or other immunologically active portion of an antibody) or primers (e.g., oligonucleotides that can be used in PCR-based assays) and, optionally, instructions for using these probes or primers to detect Wnt5a mRNA or protein in a sample. Such kits are useful in the diagnostic or screening methods described herein. Alternatively, the kits can include a pharmaceutical composition that includes Wnt5a (or a biologically active fragment or other mutant thereof), a nucleic acid encoding a Wnt5a (or a biologically active fragment or other mutant thereof) polypeptide, a small molecule activator of the Wnt5a pathway, a peptidomimetic of Wnt5a, or a chemical entity capable of activating a Wnt5a pathway (e.g., the Wnt/$Ca^{++}$ pathway).

As used herein, the term "blood cell" includes both mature and immature blood cells, e.g., hematopoietic precursor cells, lymphoid cells, or myeloid cells. For example, the blood cells can be B cells, T cells, eosinophils, basophils, erythrocytes, neutrophils, granulocytes, or monocytes. Typically, a blood cell is a B cell.

Although methods and materials similar or equivalent to those described herein can be used in the practice or testing of the present invention, suitable methods and materials are described below. All publications, patent applications, patents, and other references mentioned herein are incorporated by reference in their entirety. The materials, methods, and examples are illustrative only and not intended to be limiting. Other features and advantages of the invention will be apparent from the following detailed description, the drawings, and the claims.

BRIEF DESCRIPTION OF THE DRAWINGS

FIG. 8A is a hematoxylin and eosin-stained section of a B cell lymphoma; FIG. 8B is a B220 antibody-stained section of a B cell lymphoma; FIG. 8C is a hematoxylin and eosin-stained section of chronic myeloid leukemia; and FIG. 8D is a B220 antibody-stained section of chronic myeloid leukemia.

FIGS. 17A-17F are graphs illustrating the results of flow cytometric analysis of bone marrow (BM) or mature follicular B cells in the spleens of mice transplanted with wild type (Wnt5a+/+) FL cells (17A-17C) or Wnt5a null (Wnt5a–/–) FL cells (17D-17F), stained with combinations of anti-B220, anti-CD43, or anti-IgD antibodies.

FIG. 18 is a bar graph illustrating the results depicted in FIGS. 17A-17F, in absolute numbers.

DETAILED DESCRIPTION

Wnt5a is a member of the Wnt family of secreted glycoproteins that play essential organizing roles in development. Similar to other Wnt members, Wnt5a can upregulate cell proliferation and has been proposed to have oncogenic function. Wnt5a hemizygous mice develop myeloid leukemias and B cell lymphomas that are clonal in origin, and display loss of Wnt5a function in tumor tissues. Furthermore, analysis of human primary leukemias reveals deletion of the WNT5a gene and/or loss of WNT5A expression in a majority of the subject samples. These results demonstrate that Wnt5a suppresses hematopoietic malignancies.

Figure 1:
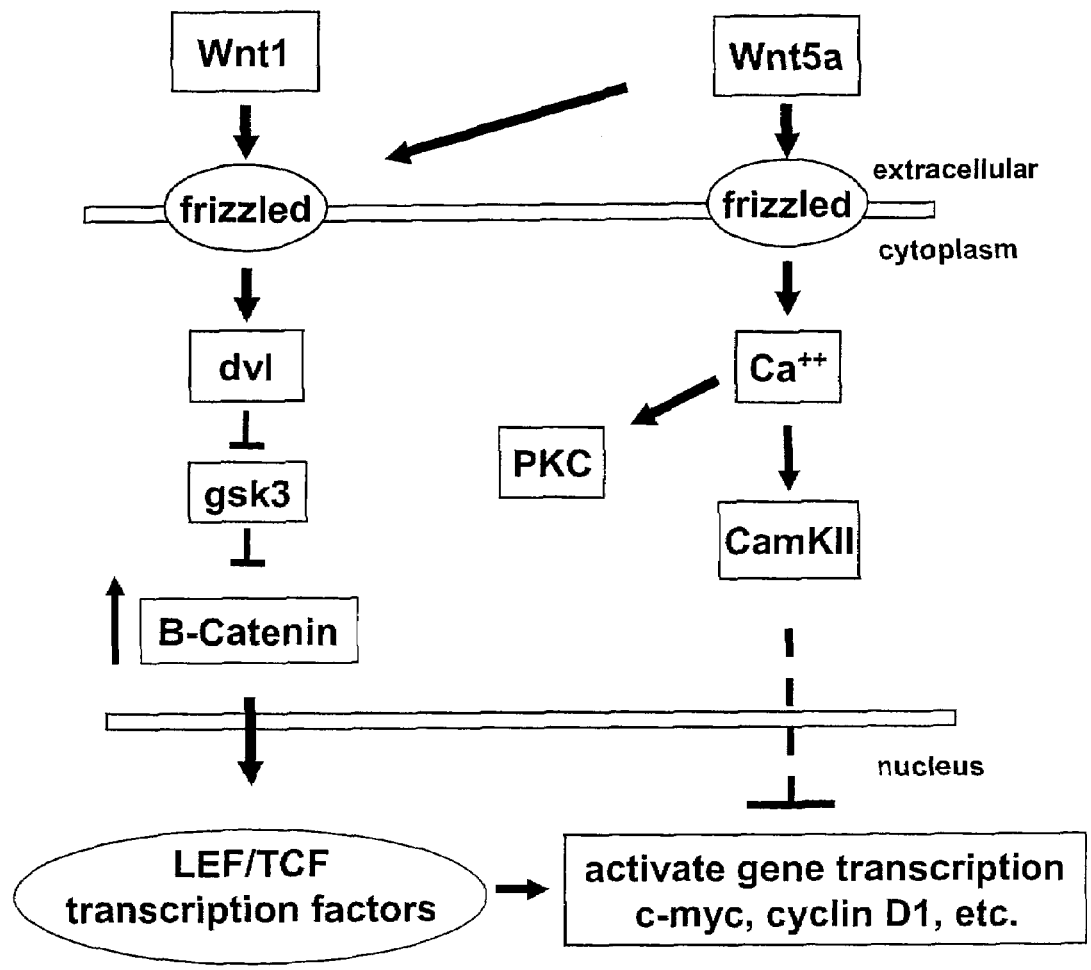
FIG. 1 is a schematic representation of Wnt1 and Wnt5a signaling pathways.

As demonstrated herein, Wnt5a is widely expressed in murine hematopoietic tissues, and, as described herein, Wnt5a signals through a non-canonical Wnt/Ca++ pathway to suppress cyclin D1 expression and negatively regulate B cell proliferation in a cell-autonomous manner (FIG. 1), by negatively regulating the response of B cells to IL-7 and suppressing cyclin D1 expression. Loss of Wnt5a does not alter β-catenin levels, but leads to a reduction in CamK II activity and in the level of phosphorylated PKC, resulting in increased expression of cyclin D1. Furthermore, a subset of Wnt5a heterozygous mice develop either spontaneous B cell lymphoma that is clonal in origin or chronic myeloid leukaemia, and tumors arising in the Wnt5a heterozygous mice display loss of Wnt5a function. Finally, analysis of primary tumors isolated from subjects with acute lymphocytic leukemia and acute myeloid leukemia reveals loss of WNT5a and WNT5a gene expression in a majority of these human samples. These results indicate that Wnt5a functions in a cell autonomous manner to negatively regulate B cell proliferation, and thus suppresses hematopoietic malignancies.

The new methods and compositions described herein are based, in part, on studies that have established Wnt5a as a tumor suppressor in B cells of two mammalian species (the present experiments were conducted in mice and humans and there is no reason to expect that the findings are not applicable to all Wnt5a-expressing cells and animals). Accordingly, increasing the expression or activity of Wnt5a can reduce the risk that a subject (e.g., a human patient) will develop a hematopoietic cancer and is, in addition, beneficial after a hematopoietic cancer is suspected or detected. Compositions that effect this increase (e.g., pharmaceutically acceptable compositions that activate the Wnt5a pathway (see FIG. 1)) can reduce the number of malignant cells (resulting in, for example, regression or remission), inhibit the rate of cellular proliferation or growth, or otherwise impact the hematopoietic cancer in a desirable way. These compositions, and kits that contain one or more of them, are described further below. We note here that the compositions can include, but are not limited to, nucleic acids that encode Wnt5a or biologically active fragments or mutants thereof, Wnt5a polypeptides or biologically active fragments or mutants thereof (wherever Wnt5a nucleic acids and polypeptides are referred to, biologically active fragments or mutants thereof are also implied; for readability, this phrase will not be repeated in every instance), Wnt5a receptor agonists, or any agent that activates the Wnt5a/Ca$^{++}$ pathway.

The new methods described herein include methods of treating hematopoietic cancers by administering a therapeutically effective amount of Wnt5a to a subject, or to cells removed from a subject (e.g., B cells) and intended to be returned to the subject, the administration being sufficient to increase the level of Wnt5a to the extent necessary to provide a therapeutic benefit to, or to prevent or reduce the risk of, hematopoietic cancer).

Also included are methods for determining whether a subject has, or is at risk of developing, a hematopoietic cancer associated with a reduction in Wnt5a expression or activity (i.e., diagnostic methods). As laboratories or other clinical-based businesses could be contracted to provide physicians or other health care professionals with information on which such a determination (e.g., a diagnosis or prognosis) could be made, the methods can also optionally or alternatively include the steps of (a) providing a biological sample comprising a test cell (or cell extract) from the subject, the test cell being of a type that normally expresses Wnt5a (e.g., a blood cell such as a B cell); (b) determining the level of Wnt5a expression or activity within the test cell (or extract), and (c) communicating the level of Wnt5a expression to a physician or other health care provider. A reduction in the level of Wnt5a expression or activity in the test cell, relative to that in a control cell, indicates that the subject has, or is at risk of developing, a hematopoietic cancer (e.g., leukemia (e.g., chronic leukemia or acute leukemia, e.g., acute myeloid leukemia or acute lymphoblastic leukemia), lymphoma (e.g., Hodgkin's and non-Hodgkin's Lymphoma, e.g., B cell lymphoma, Burkitt's lymphoma, diffuse cell lymphoma, follicular lymphoma, immunoblastic large cell lymphoma, lymphoblastic lymphoma, mantle cell lymphoma, mycosis fungoides, post-transplantation lymphoproliferative disorder, small non-cleaved cell lymphoma, and T-cell lymphoma) or myeloma).

Other methods described herein include methods of identifying anti-cancer agents. In some embodiments, these methods can be carried out by, for example, exposing a sample comprising a cell, e.g., a Wnt5a-expressing cell (e.g., a blood cell such as a B cell) to a test compound and determining the level of Wnt5a expression or activity in the Wnt5a-expressing cell. An increase in Wnt5a expression or activity, relative to the level of Wnt5a expression or activity in a control cell, indicates that the test compound is an anti-cancer agent. In some embodiments, the cell is a type of cell that typically expresses Wnt5a (e.g., a B cell), but does not express Wnt5a, e.g., a cell derived from a subject (e.g., an experimental animal or human subject) having a disorder associated with a reduction in the levels of Wnt5a, e.g., a B cell derived from a subject with a hematopoietic cancer, or an experimental animal. In some embodiments, the method includes determining the effect of the test compound on cell proliferation, in addition to, or in an alternative to, determining the effect of the test compound on Wnt5a levels.

Other methods described herein include methods of identifying hematopoietic carcinogens, e.g., agents that increase the risk that a subject will develop a hematopoietic cancer. In some embodiments, these methods can be carried out by, for example, exposing a sample comprising a Wnt5a-expressing cell (e.g., a blood cell such as a B cell) to a test compound and determining the level of Wnt5a expression or activity in the Wnt5a-expressing cell; a decrease in Wnt5a expression or activity, relative to the level of Wnt5a expression or activity in a control cell, indicates that the test compound is a carcinogen.

Screening Methods

The new methods (or "screening assays") can be used to identify test agents (a broad term that encompasses any class of substance or molecule) that bind to or otherwise modulate (i.e., stimulate or inhibit) the expression or activity of a Wnt5a nucleic acid, the protein it encodes, and/or genes or proteins that participate in the Wnt5a/Ca$^{++}$ pathway. The agents screened may be, for example, proteins, polypeptides, or peptides (these terms each describing an amino acid-based polymer) or analogs thereof, peptidomimetics (e.g., peptoids), polynucleotides or analogs thereof, other organic or inorganic compounds (e.g., heteroorganic or organometallic compounds), or naturally occurring or synthetic chemicals. In some embodiments, these agents can have a molecular weight of less than about 10,000 (e.g., about 5,000, 1,000, or 500) grams per mole and can be a salt, ester, or other pharmaceutically acceptable form of a compound.

Agents identified in the "screening" methods can be used to, for example, modulate the expression or activity of Wnt5a. As demonstrated herein, Wnt5a is a hematologic tumor suppressor, thus, agents that upregulate its expression or activity are (or are at least identified as potential or candidate) anti-cancer agents. While these agents are not limited to those that act by any particular mechanism, they may trigger apoptosis, thereby reducing the number of malignant cells (and resulting in, for example, regression or remission) or inhibit the rate of cellular proliferation or undesirable cell growth. The agents identified by virtue of their ability to alter Wnt5a expression or activity (or to otherwise affect the Wnt5a pathway) are thus useful as chemotherapeutic agents and can also be used to prevent the occurrence of a cancer or reduce a subject's risk of developing cancer (depressed levels of Wnt5a expression or activity signal an increased risk). In addition, these agents are useful in experiments designed to discover more about the biological function and clinical utility of Wnt5a.

Other "screening" methods can be carried out to identify carcinogens. These methods can be carried out by, for example, exposing a sample comprising a Wnt5a-expressing cell to a test compound and determining the level of Wnt5a expression or activity in the Wnt5a-expressing cell. A decrease in Wnt5a expression or activity, relative to the level of Wnt5a expression or activity in a control cell, indicates that the test compound is a carcinogen. Such carcinogens can be used, e.g., as rodenticides or as test agents in other assays. Where the test compound that proves to be a carcinogen is a therapeutic agent for the treatment of a non-hematopoietic cancer, the test compound can be used in combination with an agent that prevents or counteracts its action in hematopoietic cells (e.g., blood cells).

In any of these methods, the Wnt5a-expressing cell and/or the control cell can be a human cell (e.g., a primary human cell or a cell from a human cell line (e.g., a line derived from a human hematopoietic cancer). Regardless of species, the cells can also be hematopoietic cells and, more specifically, can be blood cells, e.g., lymphoid or myeloid cells. For example, the screening methods described herein can be carried out with B cells, T cells, eosinophils, basophils, erythrocytes, neutrophils, granulocytes, or monocytes. Typically, the methods will be carried out with B cells. Moreover, these cells can be tested in vitro, in cell culture, in vivo, or in a combination of environments. For example, a test cell (and/or a control cell) can be exposed to a test agent in vivo, then placed in culture before determining the level of expression or activity of Wnt5a. Similarly, a test cell (and/or control cell) can be harvested from a subject and expanded in culture before being exposed to the test agent. In some embodiments, the methods can be carried out on cells that naturally express Wnt5a, but they can also be carried out on cells that are engineered and made to express (or overexpress) Wnt5a (a full-length Wnt5a or a biologically active fragment or other mutant thereof).

While Wnt5a expression or activity can be assessed in a single cell, it is expected that the methods described herein will typically be carried out using populations (including mixed populations) of cells. Where the level of Wnt5a expression or activity is determined in more than one Wnt5a-expressing cell and in more than one control cell, the average level of expression in the Wnt5a-expressing cells can be compared to the average level of expression in the control cells.

Numerous techniques are available to assess Wnt5a expression or activity. These techniques include any known methods for examining genomic DNA, mRNA, or protein expression. Typically, genomic DNA is evaluated using methods in which genomic DNA from the test cell is exposed to a Wnt5a-specific nucleic acid primer or probe, e.g., in southern hybridization or PCR-based assays. In some embodiments, mRNA is detected by methods in which Wnt5a mRNA from the test cell is exposed to a Wnt5a-specific nucleic acid primer or probe (e.g., an oligonucleotide, as can be used in Northern blot analysis, RNAse protection assays, or PCR-based assays). In some embodiments, protein is detected using Wnt5a-specific antibodies (i.e., by way of an immunoassay, e.g., immunoprecipitation or Western blotting).

The level of Wnt5a activity can also be determined by assessing the level of expression or activity of a component of the Wnt5a pathway that lies downstream of Wnt5a in the Wnt5a pathway (e.g., downstream of receptor activation). For example, one can assess the level of expression or activity of cyclin D1 and/or assess the extent of phosphorylation of protein kinase C (PKC), calmodulin kinase II (CamK II), dishevelled (dvl), c-Jun, or LEF-1.

The agents screened can be obtained from combinatorial libraries. Methods known in the art allow the production and screening of: biological libraries; peptoid libraries (i.e., libraries of molecules that function as peptides even though they have a non-peptide backbone that confers resistance to enzymatic degradation; see, e.g., Zuckermann et al., *J. Med. Chem.* 37:2678-85, 1994); spatially addressable parallel solid phase or solution phase libraries; synthetic libraries requiring deconvolution; "one-bead one-compound" libraries; and synthetic libraries. The biological and peptoid libraries can be used to test only peptides, but the other four are applicable to testing peptides, non-peptide oligomers or libraries of small molecules (Lam, *Anticancer Drug Des.* 12:145, 1997). Molecular libraries can be synthesized as described by DeWitt et al. (*Proc. Natl. Acad. Sci. USA* 90:6909, 1993) Erb et al. (*Proc. Natl. Acad. Sci. USA* 91:11422, 1994) Zuckermann et al. (*J. Med. Chem.* 37:2678, 1994) Cho et al. (*Science* 261: 1303, 1993) and Gallop et al. (*J. Med. Chem.* 37:1233, 1994).

Libraries of compounds can be presented in solution (see, e.g., Houghten, *Biotechniques* 13:412-421, 1992), or on beads (Lam, *Nature* 354:82-84, 1991), chips (Fodor, *Nature* 364:555-556, 1993), bacteria or spores (U.S. Pat. No. 5,223, 409), plasmids (Cull et al., *Proc. Natl. Acad. Sci. USA* 89:1865-1869, 1992) or on phage (Scott and Smith, *Science* 249:386-390, 1990; Devlin, *Science* 249:404-406, 1990; Cwirla et al., *Proc. Natl. Acad. Sci. USA* 87:6378-6382, 1990; Felici, *J. Mol. Biol.* 222:301-310, 1991; and U.S. Pat. No. 5,223,409).

Alternatively, or in addition to examining the ability of an agent to modulate expression or activity generally, one can examine the ability of an agent to interact with (by, for example, specifically binding), Wnt5a or a nucleic acid molecule that encodes Wnt5a. For example, one can couple an agent to a label (e.g., radioactive or enzymatically active substances), contact Wnt5a, or a nucleic acid molecule that encodes it, with the labeled agent, and determine whether they bind one another (by detecting, for example, a complex containing the nucleic acid or protein and the labeled agent). Labels are not, however, always required. For example, one can use a microphysiometer to detect interaction between an agent and a protein described herein, neither of which were previously labeled (McConnell et al., *Science* 257:1906-1912, 1992). A micro-physiometer (also known as a cytosensor) is an analytical instrument that measures the rate at which a cell acidifies its environment. The instrument uses a light-addressable potentiometric sensor (LAPS), and changes in the acidification rate indicate interaction between an agent and a protein described herein. Molecular interactions can also be detected using fluorescence energy transfer (FET; see, e.g., U.S. Pat. Nos. 5,631,169 and 4,868,103). An FET binding event can be conveniently measured through fluorometric detection means well known in the art (e.g., by means of a fluorimeter). Where analysis in real time is desirable, one can examine the interaction (e.g., binding) between an agent and a protein described herein with Biomolecular Interaction Analysis (BIA; see, e.g., Sjolander and Urbaniczky *Anal.*

Chem. 63:2338-2345, 1991 and Szabo et al., *Curr. Opin. Struct. Biol.* 5:699-705, 1995). BIA allows one to detect biospecific interactions in real time without labeling any of the interactants (e.g., BIAcore).

One can also screen for anti-cancer agents or carcinogens in cell-free assays (i.e., soluble or membrane-bound forms of Wnt5a, including variants, mutants, and other fragments, can be used to identify agents that bind those proteins or otherwise modulate their expression or activity). The basic protocol is the same as that for a cell-based assay in that, in either case, one must contact Wnt5a or a nucleic acid that encodes it with an agent of interest (for a sufficient time and under appropriate (e.g., physiological) conditions to allow any potential interaction to occur) and then determine whether the agent binds the protein or nucleic acid or otherwise modulates their expression or activity. When membrane-bound forms of the protein are used, it may be desirable to utilize a solubilizing agent (e.g., non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate).

Any Wnt5a protein or any of the agents being tested can be anchored to a solid phase or otherwise immobilized (assays in which such anchoring occurs are sometimes referred to as "heterogeneous" assays). For example, a Wnt5a protein can be anchored to a microtiter plate, a test tube, a microcentrifuge tube, a column, or the like before it is exposed to an agent. Any complex that forms on the solid phase is detected at the end of the period of exposure. For example, Wnt5a can be anchored to a solid surface, and the test compound (which is not anchored and can be labeled, directly or indirectly) is added to the surface bearing the anchored protein. Un-reacted (e.g., unbound) components can be removed (by, e.g., washing) under conditions that allow any complexes formed to remain immobilized on the solid surface, where they can be detected (e.g., by virtue of a label attached to the protein or the agent or with a labeled antibody that specifically binds an immobilized component and may, itself, be directly or indirectly labeled).

One can immobilize either Wnt5a or an antibody to which it specifically binds to facilitate separation of complexed (or bound) protein from uncomplexed (or unbound) protein. Such immobilization can also make it easier to automate the assay, and fusing Wnt5a to heterologous proteins can facilitate their immobilization. For example, proteins fused to glutathione-S-transferase can be adsorbed onto glutathione sepharose beads (Sigma Chemical Co., St. Louis, Mo.) or glutathione derivatized microtiter plates, then combined with the agent and incubated under conditions conducive to complex formation (e.g., conditions in which the salt and pH levels are within physiological levels). Following incubation, the solid phase is washed to remove any unbound components (where the solid phase includes beads, the matrix can be immobilized), the presence or absence of a complex is determined. Alternatively, complexes can be dissociated from a matrix, and the level of protein binding or activity can be determined using standard techniques.

Immobilization can be achieved with methods known in the art. For example, biotinylated protein can be prepared from biotin-NHS (N-hydroxy-succinimide) using techniques known in the art (e.g., the biotinylation kit from Pierce Chemicals, Rockford, Ill.) and immobilized in the wells of streptavidin-coated tissue culture plates (also from Pierce Chemical).

Cell-free assays can also be conducted in a liquid phase, in which case any reaction product can be separated (and thereby detected) by, for example: differential centrifugation (Rivas and Minton, *Trends Biochem Sci* 18:284-7, 1993); chromatography (e.g., gel filtration or ion-exchange chromatography); electrophoresis (see, e.g., Ausubel et al., Eds., *Current Protocols in Molecular Biology*, J. Wiley & Sons, New York, N.Y., 1999); or immunoprecipitation (see, e.g., Ausubel et al. (supra); see also Heegaard, *J. Mol. Recognit.* 111:141-148, 1998 and Hage and Tweed, *J. Chromatogr. Biomed. Sci. Appl.* 699:499-525, 1997). Fluorescence energy transfer (see above) can also be used, and is convenient because binding can be detected without purifying the complex from solution. Assays in which the entire reaction of interest is carried out in a liquid phase are sometimes referred to as homogeneous assays.

The screening methods described herein can also be designed as competition assays in which a test agent and a substance that is known to bind Wnt5a compete to bind Wnt5a. Depending on the order of addition of reaction components and the reaction conditions (e.g., whether the reaction is allowed to reach equilibrium), agents that inhibit complex formation can be distinguished from those that disrupt preformed complexes. In either approach, the order in which reactants are added can be varied to obtain different information about the agents being tested. For example, agents that interfere with the interaction between a gene product and one or more of its binding partners (by, e.g., competing with the binding partner), can be identified by adding the binding partner and the agent to the reaction at about the same time. Agents that disrupt preformed complexes (by, e.g., displacing one of the components from the complex), can be added after a complex containing the gene product and its binding partner has formed.

The proteins described herein can also be used as "bait proteins" in a two- or three-hybrid assay (see, e.g., U.S. Pat. No. 5,283,317; Zervos et al., *Cell* 72:223-232, 1993; Madura et al., *J. Biol. Chem.* 268:12046-12054, 1993; Bartel et al. *Biotechniques* 14:920-924, 1993; Twabuchi et al., *Oncogene* 8:1693-1696, 1993; and WO 94/10300) to identify other proteins that bind to (e.g., specifically bind to) or otherwise interact with Wnt5a. Such binding proteins can activate or inhibit the proteins described herein (and thereby influence the biochemical pathways and events in which those proteins are active).

Of course, two or more of the methods described herein can be practiced together. For example, one can evaluate an agent that was first identified in a cell-based assay in a cell free assay. Similarly, the ability of the agent to modulate the expression or activity of Wnt5a can be confirmed in vivo.

Monitoring the influence of therapeutic agents (e.g., chemotherapeutics) or other events (e.g., radiation therapy) on the expression or activity of Wnt5a can be useful in clinical trials (a desired extension of the screening assays described above). For example, agents that exert an effect by, in part, altering the expression or activity of Wnt5a ex vivo can be tested for their ability to do so as the treatment progresses in a subject. Moreover, in animal or clinical trials, the expression or activity of a nucleic acid can be used, optionally in conjunction with that of other genes, as a "read out" or a marker of the phenotype of a particular cell.

Diagnostics and Predictive Medicine

The compositions described herein (e.g., the Wnt5a nucleic acids and proteins, agents that specifically bind them, and cells that contain them) are generally useful in the field of predictive medicine and are, more specifically, useful in diagnostic and prognostic assays and in monitoring clinical trials. For example, one can determine whether a subject is at risk of developing a disorder associated with misexpression (i.e., a level of expression that is statistically below a normal level) of Wnt5a (e.g., leukemia (e.g., chronic leukemia or acute leukemia, e.g., acute myeloid leukemia or acute lymphoblastic leukemia), lymphoma (e.g., Hodgkin's and non-Hodgkin's Lymphoma, e.g., B cell lymphoma, Burkitt's lymphoma, diffuse cell lymphoma, follicular lymphoma, immunoblastic large cell lymphoma, lymphoblastic lymphoma, mantle cell lymphoma, mycosis fungoides, post-transplantation lymphoproliferative disorder, small non-cleaved cell lymphoma, and T-cell lymphoma), and myeloma). Nucleic acids differentially expressed in malignant cells (e.g., a nucleic acid encoding a Wnt5a transcriptional downregulator) can serve as indicators that a subject has, or is likely to develop, a cancer associated with decreased Wnt5a expression (e.g., leukemia (e.g., chronic leukemia or acute leukemia, e.g., acute myeloid leukemia or acute lymphoblastic leukemia), lymphoma (e.g., Hodgkin's and non-Hodgkin's Lymphoma, e.g., B cell lymphoma, Burkitt's lymphoma, diffuse cell lymphoma, follicular lymphoma, immunoblastic large cell lymphoma, lymphoblastic lymphoma, mantle cell lymphoma, mycosis fungoides, post-transplantation lymphoproliferative disorder, small non-cleaved cell lymphoma, and T-cell lymphoma), and myeloma). The absence of one or more Wnt5a alleles in the genomic DNA of a subject can also serve as an indicator that a subject has, or is likely to develop, a cancer associated with decreased Wnt5a expression (e.g., leukemia (e.g., chronic leukemia or acute leukemia, e.g., acute myeloid leukemia or acute lymphoblastic leukemia), lymphoma (e.g., Hodgkin's and non-Hodgkin's Lymphoma, e.g., B cell lymphoma, Burkitt's lymphoma, diffuse cell lymphoma, follicular lymphoma, immunoblastic large cell lymphoma, lymphoblastic lymphoma, mantle cell lymphoma, mycosis fungoides, post-transplantation lymphoproliferative disorder, small non-cleaved cell lymphoma, and T-cell lymphoma), and myeloma).

For example, in some embodiments, one can assess expression of Wnt5a by isolating Wnt5a mRNA or protein from a cell or population of cells (either of which may be referred to herein as a "sample"), e.g., blood cells such as B cells, and comparing the amount of Wnt5a mRNA or protein isolated from the sample to the amount of Wnt5a mRNA or protein, respectively, in a control cell or population of cells (e.g., a comparable cell or population of cells obtained from the same subject at an earlier time; obtained from another subject; or obtained from either the same or a different subject following exposure to a chemotherapeutic agent or other test compound). Wnt5a mRNA or protein can be isolated in a number of ways. For example, it can be isolated by standard biochemical techniques, including those that require electrophoresis through a semi-solid medium (e.g., an agarose gel) and transfer to a solid support (e.g., a nylon membrane). Wnt5a mRNA can also be assessed in PCR-based assays. In any event, the extent of isolation need only be sufficient to determine the level (or relative level) of Wnt5a expression. Highly purified samples are not required. The significance of the level of Wnt5a expression can vary. For example, where Wnt5a is assessed in cells from the same subject at different points in time, an increase in Wnt5a (expression or activity) will indicate that the subject's risk of cancer has decreased; conversely, a decrease in Wnt5a will suggest an increase in their susceptibility. Similarly, where Wnt5a expression is increased in the presence of a test compound, one can conclude that the test compound deserves further testing as (or may be) an anti-cancer agent or a prophylactic agent. Other scenarios are discussed below. The sample provided for any of these methods can include human cells or cells from the other animals listed above.

A physician or other health care provider can determine the level of Wnt5a expression or activity in a sample and make a diagnosis or suggest a treatment regime based on that level. Alternatively, a technician can make the determination and provide the results to another entity (e.g., a physician or health care provider). Of course, the results may be useful for more than diagnostic or therapeutic purposes; they may also serve to further elucidate the function, properties, or utility of Wnt5a in different tissues or cell types or under different conditions. For example, the levels of Wnt5a expression or activity can be used to determine (or help determine) whether Wnt5a serves as a tumor suppressor in a certain type of cancer (e.g., a hematopoietic cancer such as leukemia (e.g., chronic leukemia or acute leukemia, e.g., acute myeloid leukemia or acute lymphoblastic leukemia), lymphoma (e.g., Hodgkin's and non-Hodgkin's Lymphoma, e.g., B cell lymphoma, Burkitt's lymphoma, diffuse cell lymphoma, follicular lymphoma, immunoblastic large cell lymphoma, lymphoblastic lymphoma, mantle cell lymphoma, mycosis fungoides, post-transplantation lymphoproliferative disorder, small non-cleaved cell lymphoma, and T-cell lymphoma), or myeloma).

As noted, the "subject" or "patient" referred to here, and that referred to in the context of any of the methods described herein, is any animal that normally expresses Wnt5a (e.g., a mammal such as an animal commonly used in experimental studies (e.g., rats, mice, rabbits and guinea pigs); a domesticated animal (e.g., a dog or cat); an animal kept as livestock (e.g., a pig, cow, sheep, goat, or horse); a non-human primate (e.g. an ape, monkey, or chimpanzee); a human; an avian (e.g., a chicken); an amphibian (e.g., a frog); or a reptile. As the subject or patient can be an unborn animal, the methods described herein can be used to carry out genetic screening, to make prenatal diagnoses, or administer a treatment.

The mere presence or absence of Wnt5a transcripts, which are differentially expressed in the event of a pathological condition (cancer) is informative and useful (both for diagnosing a condition and making a prognosis concerning it). One can use all or a part of a nucleic acid that encodes Wnt5a to detect, for example, in a tissue of a subject:

(1) a mutation that affects the expression of the Wnt5a gene (e.g., a mutation in the 5' regulatory region of a Wnt5a gene allele, or a deletion of all or part of a Wnt5a allel);
(2) a mutation that alters the structure of the Wnt5a gene;
(3) an altered level (i.e., a non-wild type level, e.g., a reduced level) of mRNA for the Wnt5a gene (the proteins described herein can be similarly used to detect an altered level of protein expression);
(4) a deletion or addition of one or more nucleotides from Wnt5a;
(5) a substitution of one or more nucleotides in Wnt5a gene (e.g., a point mutation), e.g., a substitution that alters the structure and/or biological function of the Wnt5a protein, e.g., a non-conservative substitution;
(6) a gross chromosomal rearrangement (e.g., a translocation, inversion, or deletion); or
(7) aberrant modification of the Wnt5a gene (e.g., modification of the methylation pattern of the genomic DNA).

Similarly, one can test for inappropriate post-translational modification of any protein encoded (e.g., inappropriate glycosylation or an inability to be secreted from the cell). Abnormal expression, abnormal gene or abnormal protein structures indicate that the subject is at risk for an associated disorder (e.g., a leukemia (e.g., chronic leukemia or acute leukemia, e.g., acute myeloid leukemia or acute lymphoblastic leukemia), lymphoma (e.g., Hodgkin's and non-Hodgkin's Lymphoma, e.g., B cell lymphoma, Burkitt's lymphoma, diffuse cell lymphoma, follicular lymphoma, immunoblastic large cell lymphoma, lymphoblastic lymphoma, mantle cell lymphoma, mycosis fungoides, post-transplantation lymphoproliferative disorder, small non-cleaved cell lymphoma, and T-cell lymphoma), and myeloma). Once a subject has been identified as at risk for, or having an associated disorder, the subject can be treated, e.g., by administering a therapeutically effective amount of a composition comprising an agent that increases Wnt5a levels, e.g., Wnt5a protein and/or nucleic acid levels, e.g., a Wnt5a pharmaceutical composition as described herein.

Additionally, the level of Wnt5a protein and/or nucleic acid can likely be used to stage associated disorders, with lower levels (e.g., the complete absence) of Wnt5a correlating with more aggressive disease, and a poorer clinical outcome.

A genetic lesion can be detected by, for example, providing an oligonucleotide probe or primer having a sequence that hybridizes to a sense or antisense strand of the Wnt5a gene, a naturally occurring mutant thereof, or the 5' or 3' sequences that are naturally associated with the corresponding gene and exposing the probe or primer to a nucleic acid within a tissue of interest (e.g., a tumor). One can detect hybridization between the probe or primer and the nucleic acid of the tissue by standard methods (e.g., in situ hybridization) and thereby detect the presence or absence of the genetic lesion. Where the probe or primer specifically hybridizes with a new splice variant, the probe or primer can be used to detect a non-wildtype splicing pattern of the mRNA. The antibodies described herein can be similarly used to detect the presence or absence of a protein encoded by a mutant, misexpressed, or otherwise deficient gene. Methods suitable for use in the diagnostic and prognostic assays are known in the art and are described herein.

Detection Methods

Qualitative or quantitative analyses (which reveal the presence or absence of a substance or its level (or relative level) of expression or activity, respectively) can be carried out for the Wnt5a gene or the protein it encodes, by obtaining a biological sample (e.g., a sample comprising a cell, e.g., a blood cell, or an extract thereof) from a subject and contacting the sample with an agent capable of specifically binding a nucleic acid represented by the Wnt5a gene or a protein encoded by the Wnt5a gene. The conditions in which the contact is made should allow for specific binding. The biological sample can be a tissue, a cell, or a bodily fluid (e.g., bone marrow, blood or serum), which may or may not be extracted from the subject (i.e., expression can be monitored in vivo). More specifically, the expression of a nucleic acid sequence can be examined by, for example, Southern or Northern analyses, polymerase chain reaction analyses, or with probe arrays. For example, one can diagnose a condition associated with expression or misexpression of a gene by isolating mRNA from a cell and contacting the mRNA with a nucleic acid probe with which it can hybridize under stringent conditions (the characteristics of useful probes are known to those of ordinary skill in the art and are discussed elsewhere herein). The mRNA can be immobilized on a surface (e.g., a membrane, such as nitrocellulose or other commercially available membrane) following gel electrophoresis.

Alternatively, one or more nucleic acids (the target sequence or the probe) can be distributed on a two-dimensional array (e.g., a gene chip). Arrays are useful in detecting mutations because a probe positioned on the array can have one or more mismatches to a nucleic acid described herein (e.g., a destabilizing mismatch). For example, a genetic mutation of the Wnt5a gene can be identified in two-dimensional arrays containing light-generated DNA probes (Cronin et al., *Human Mutation* 7:244-255, 1996) (similarly, one can construct an array including some or all of any subset of these nucleic acids, such as some or all of the nucleic acids differentially expressed in lymphoid or myeloid cells). Briefly, when a light-generating (e.g., fluorescent) DNA probe is used, a first array of probes is used to scan through long stretches of DNA in a sample and a control to identify base changes between the sequences by making linear arrays of sequential overlapping probes. This step allows the identification of point mutations, and it can be followed by use of a second array that allows the characterization of specific mutations by using smaller, specialized probe arrays complementary to all variants or mutations detected. Each mutation array is composed of parallel probe sets, one complementary to the wild-type gene and the other complementary to the mutant gene. Arrays are discussed further below; see also; Kozal et al. *Nature Medicine* 2:753-759, 1996).

The level of Wnt5a mRNA in a sample can also be evaluated with a nucleic acid amplification technique (e.g., RT-PCR (U.S. Pat. No. 4,683,202), ligase chain reaction (LCR; Barany, *Proc. Natl. Acad. Sci. USA* 88:189-193, 1991; LCR can be particularly useful for detecting point mutations), self-sustained sequence replication (Guatelli et al., *Proc. Natl. Acad. Sci. USA* 87:1874-1878, 1990), transcriptional amplification system (Kwoh et al., *Proc. Natl. Acad. Sci. USA* 86:1173-1177, 1989), Q-Beta Replicase (Lizardi et al., *Bio/Technology* 6:1197, 1988), or rolling circle replication (U.S. Pat. No. 5,854,033)). Following amplification, the nucleic acid can be detected using techniques known in the art. Amplification primers are a pair of nucleic acids that anneal to 5' or 3' regions of a gene (plus and minus strands, respectively, or vice-versa) at some distance (and possibly a short distance) from one another. For example, each primer can consist of about 10 to 30 nucleotides and bind to sequences that are about 50 to 200 nucleotides apart. Serial analysis of gene expression can be used to detect transcript levels (U.S. Pat. No. 5,695,937). Other useful amplification techniques (useful in, for example, detecting an alteration in a gene) include anchor PCR or Rapid Amplification of cDNA Ends (RACE) PCR.

Mutations in the gene sequences described herein can also be identified by examining alterations in restriction enzyme cleavage patterns. For example, one can isolate DNA from a sample cell or tissue and a control, amplify it (if necessary), digest it with one or more restriction endonucleases, and determine the length(s) of the fragment(s) produced (by, e.g., gel electrophoresis). If the size of the fragment obtained from the sample is different from the size of the fragment obtained from the control, there is a mutation in the DNA in the sample tissue. Sequence specific ribozymes (see, for example, U.S. Pat. No. 5,498,531) can be used to detect specific mutations by development or loss of a ribozyme cleavage site.

Any of the variety of sequencing reactions known in the art (including those that are automated) can also be used to determine whether there is a mutation, and, if so, how the mutant differs from the wild type sequence. Mutations can also be identified by using cleavage agents to detect mismatched bases in RNA/RNA or RNA/DNA duplexes (Myers et al., *Science* 230:1242, 1985; Cotton et al., *Proc. Natl. Acad. Sci. USA* 85:4397, 1988; Saleeba et al., *Methods Enzymol.* 217:286-295, 1992). Mismatch cleavage reactions employ one or more proteins that recognize mismatched base pairs in double-stranded DNA (so called "DNA mismatch repair" enzymes; e.g., the mutY enzyme of *E. coli* cleaves A at G/A mismatches and the thymidine DNA glycosylase from HeLa cells cleaves T at G/T mismatches (see Hsu et al., *Carcinogenesis* 15:1657-1662, 1994 and U.S. Pat. No. 5,459,039).

Alterations in electrophoretic mobility can also be used to identify mutations. For example, single strand conformation polymorphism (SSCP) can be used to detect differences in electrophoretic mobility between mutant and wild type nucleic acids (Orita et al., *Proc. Natl. Acad. Sci. USA* 86:2766, 1989; see also *Cotton Mutat. Res.* 285:125-144, 1993; and Hayashi, *Genet. Anal Tech. Appl.* 9:73-79, 1992). Single-stranded DNA fragments of sample and control nucleic acids are denatured and allowed to renature. The secondary structure of single-stranded nucleic acids varies according to sequence, and the resulting alteration in electrophoretic mobility enables the detection of even a single base change. The sensitivity of the assay is enhanced when RNA (rather than DNA) is used because RNA's secondary structure is more sensitive to a change in sequence. See also Keen et al. (*Trends Genet.* 7:5, 1991). The movement of mutant or wild-type fragments through gels containing a gradient of denaturant is also informative.

When denaturing gradient gel electrophoresis (DGGE; Myers et al., *Nature* 313:495, 1985) is used, DNA can be modified so it will not completely denature (this can be done by, for example by adding a GC clamp of approximately 40 bp of high-melting GC-rich DNA by PCR). A temperature gradient can be used in place of a denaturing gradient to identify differences in the mobility of control and sample DNA (Rosenbaum and Reissner, *Biophys. Chem.* 265:12753, 1987).

Point mutations can also be detected by selective oligonucleotide hybridization, selective amplification, or selective primer extension (Point et al., *Nature* 324:163, 1986; Saiki et al., *Proc. Natl. Acad. Sci. USA* 86:6230, 1989) or by chemical ligation of oligonucleotides as described in Xu et al. (*Nature Biotechnol.* 19: 148, 2001). Allele specific amplification technology can also be used (see, e.g., Gibbs et al., *Nucleic Acids Res.* 17:2437-2448, 1989; Prossner, *Tibtech.* 11:238, 1993; and Barany, *Proc. Natl. Acad. Sci. USA* 88:189, 1991).

When the analysis of a gene or protein is carried out in a cell or tissue sample, the cell or tissue can be immobilized on a support, typically a glass slide, and then contacted with a probe that can hybridize to the nucleic acid or protein of interest.

The detection methods described herein can be carried out with appropriate controls (e.g., analyses can be conducted in parallel with a sample known to contain the target sequence and a target known to lack it; with a cell from a healthy subject and a cell of the same type from a subject who has a hematopoietic cancer; with a cell harvested from a subject at an earlier point in time and a cell harvested at a later point in time).

There are also a variety of methods that can be used to determine protein expression or activity. For example, one can evaluate the amount of protein in a sample by exposing the sample to an antibody that specifically binds the protein of interest or an antigen-binding fragment thereof. For example, (i) a Fab fragment (i.e., a monovalent fragment consisting of the VL, VH, CL and CH1 domains); (ii) a F(ab')$_2$ fragment (i.e., a bivalent fragment containing two Fab fragments linked by a disulfide bond at the hinge region); (iii) a Fd fragment consisting of the VH and CH1 domains; (iv) a Fv fragment consisting of the VL and VH domains of a single arm of an antibody, (v) a dAb fragment (Ward et al., *Nature* 341:544-546, 1989), which consists of a VH domain; or (vi) an isolated complementarity determining region (CDR). The antibodies can be monoclonal antibodies, and these antibodies or fragments thereof can be detectably labeled with, for example, an enzyme (e.g., horseradish peroxidase, alkaline phosphatase, β-galactosidase, or acetylcholinesterase), a prosthetic group (e.g., streptavidin/biotin and avidin/biotin), or a fluorescent, luminescent, bioluminescent, or radioactive material. (e.g., umbelliferone, fluorescein, fluorescein isothiocyanate, rhodamine, dichlorotriazinylamine fluorescein, dansyl chloride or phycoerythrin (which are fluorescent), luminol (which is luminescent), luciferase, luciferin, and aequorin (which are bioluminescent), and $^{125}$I, $^{131}$I, $^{35}$S or $^3$H (which are radioactive)).

The methods can be carried out in vitro (e.g., one can perform an enzyme linked immunosorbent assay (ELISA), an immunoprecipitation, an immunofluorescence analysis, an enzyme immunoassay (EIA), a radioimmunoassay (RIA), or a Western blot analysis) or in vivo (e.g., one can introduce a labeled antibody that specifically binds to protein encoded by the Wnt5a gene into a subject and then detect it by a standard imaging technique). Alternatively, the sample can be labeled and then contacted with an antibody. For example, one can biotinylate the sample, contact it with an antibody (e.g., an antibody positioned on an antibody array) and then detect the bound sample (e.g., with avidin coupled to a fluorescent label). As with methods to detect nucleic acids, appropriate control studies can be performed in parallel with those designed to detect protein expression.

The reagents disclosed herein can be assembled as kits. Accordingly, the invention features kits for detecting levels of Wnt5a nucleic acid, the proteins they encode, or other components of the Wnt5a pathway in a biological sample. The kit can include a probe (e.g., a nucleic acid sequence or an antibody), a standard and, optionally, instructions for use. More specifically, antibody-based kits can include a first antibody (e.g., in solution or attached to a solid support) that specifically binds a protein encoded by the Wnt5a gene and, optionally, a second, different antibody that specifically binds to the first antibody and is conjugated to a detectable agent. Oligonucleotide-based kits can include an oligonucleotide (e.g., a detectably labeled oligonucleotide) that hybridizes with the Wnt5a gene under stringent conditions or a pair of oligonucleotides that can be used to amplify a nucleic acid sequence within the Wnt5a gene. The kits can also include a buffering agent, a preservative, a protein-stabilizing agent, or a component necessary for detecting any included label (e.g., an enzyme or substrate). The kits can also contain a control sample or a series of control samples that can be assayed and compared to the test sample contained. Each component of the kit can be enclosed within an individual container, and all of the various containers can be within a single package.

In another aspect, the invention features a computer medium having a plurality of digitally encoded data records. Each data record includes a value representing the level of expression of any the Wnt5a gene in a sample, and a descriptor of the sample (e.g., an identifier, such as information about the subject from which the sample was obtained, a diagnosis made or a treatment performed in the event the level of expression reaches a certain level or falls below a certain level). The data record can also include values representing the level of expression of related genes (e.g., where the data record includes a gene that is differentially expressed in cancer cells, other genes that are expressed in cancer cells can be present as well. The data record can be structured as a table (e.g., a table that is part of a database such as a relational database (e.g., a SQL database of the Oracle or Sybase database environments).

Expression Profiling

The invention further provides methods of providing Wnt5a expression profiles. As described herein, the screening methods described herein can be used to identify candidate therapeutic agents, and those agents can be evaluated further by examining their ability to alter the expression of Wnt5a, e.g., in vivo. For example, one can obtain a cell from a subject, contact the cell with the agent, and subsequently examine the cell's Wnt5a expression profile with respect to a reference profile (which can be, for example, the profile of a normal cell or that of a cell in a physiologically acceptable condition). The agent is evaluated favorably if the expression profile in the subject's cell is, following exposure to the agent, more similar to that of a normal cell or a cell in a physiologically acceptable condition. A control assay can be performed with, for example, a cell that is not exposed to the agent. In some embodiments, the agent is a nucleic acid encoding a Wnt5a protein or biologically active fragment thereof.

Expression profiles (obtained by evaluating either nucleic acid or protein expression) are also useful in evaluating subjects. One can obtain a sample from a subject (either directly or indirectly from a caregiver), create an expression profile, and, optionally, compare the subject's expression profile to one or more reference profiles and/or select a reference profile most similar to that of the subject. A variety of routine statistical measures can be used to compare two reference profiles. One possible metric is the length of a distance vector that is the difference between the two profiles. Each of the subject and reference profile is represented as a multi-dimensional vector, wherein each dimension is a value in the profile.

The result, which can be transmitted to the subject, a caregiver, or another interested party, can be the subject expression profile per se, a result of a comparison of the subject expression profile with another profile, a most similar reference profile, or a descriptor of any of these. Transmission can occur across a computer network (e.g., in the form of a computer transmission such as a computer data signal embedded in a carrier wave). Accordingly, the invention also features a computer medium having executable code for causing a process or computer system to: receive a subject expression profile; access a database of reference expression profiles; and either i) select a matching reference profile most similar to the subject expression profile, or ii) determine at least one comparison score for the similarity of the subject expression profile to at least one reference profile. The subject expression profile and the reference expression profile each include a value representing the level of expression Wnt5a protein or nucleic acid.

In some embodiments, the expression profile can then be used to select a treatment. For example, if the subject is determined to have decreased Wnt5a protein or nucleic acid expression levels, the subject can be treated with an agent that increases Wnt5a levels.

Wnt5a Protein Expression

Wnt5a can be delivered to cells in culture or in vivo by exposing the cells to nucleic acid sequences that encode Wnt5a or biologically active fragments or other mutants thereof (such fragments or mutants will retain enough of the natural biological activity of the wildtype protein to be useful in the therapeutic, diagnostic, or screening methods described herein, e.g., are able to signal through a non-canonical Wnt5/$Ca^{++}$ pathway). The Wnt5a-encoding sequence can be a part of an expression vector, and many vectors have been designed to express proteins in prokaryotic or eukaryotic cells.

Wnt5a proteins expressed in prokaryotic cells can be purified and administered to a subject instead of, or together with, Wnt5a-expressing nucleic acids. For example, a Wnt5a polypeptide can be expressed in bacterial cells (e.g., E. coli), fungi, yeast, or insect cells (e.g., using baculovirus expression vectors). For example, a baculovirus such as Autographa californica nuclear polyhedrosis virus (AcNPV), which grows in Spodoptera frugiperda cells, can be used as a vector to express foreign genes. A Wnt5a-encoding nucleic acid can be cloned into a non-essential region (for example the polyhedrin gene) of the viral genome and placed under control of a promoter (e.g., the polyhedrin promoter). Successful insertion of the nucleic acid results in inactivation of the polyhedrin gene and production of non-occluded recombinant virus (i.e., virus lacking the proteinaceous coat encoded by the polyhedrin gene). These recombinant viruses are then typically used to infect insect cells (e.g., Spodoptera frugiperda cells) in which the inserted gene is expressed (see, e.g., Smith et al., *J. Virol.* 46:584, 1983 and U.S. Pat. No. 4,215,051). If desired, mammalian cells can be used in lieu of insect cells, provided the virus is engineered so that the nucleic acid is placed under the control of a promoter that is active in mammalian cells.

Useful mammalian cells include rodent cells, such as Chinese hamster ovary cells (CHO) or COS cells, primate cells, such as African green monkey kidney cells, rabbit cells, or pig cells). The mammalian cells can also be human cells (e.g., a hematopoietic cell, a fibroblast, or a tumor cell). For example, HeLa cells, 293 cells, 3T3 cells, and W138 cells are useful. Other suitable host cells are known to those skilled in the art and are discussed further in Goeddel (Gene Expression Technology: Methods in Enzymology 185, Academic Press, San Diego, Calif., 1990).

Wnt5a proteins can also be produced in plant cells, if desired. For plant cells, viral expression vectors (e.g., cauliflower mosaic virus and tobacco mosaic virus) and plasmid expression vectors (e.g., Ti plasmid) are suitable. These cells and other types are available from a wide range of sources (e.g., the American Type Culture Collection, Manassas, Va.; see also, e.g., Ausubel et al., *Current Protocols in Molecular Biology*, John Wiley & Sons, New York, 1994). The optimal methods of transformation (by, for example, transfection) and, as noted above, the choice of expression vehicle will depend on the host system selected. Transformation and transfection methods are described in, for example, Ausubel et al., supra; expression vehicles can be chosen from those provided in, for example, Pouwels et al., Cloning Vectors: A Laboratory Manual, 1985, Supp. 1987. The host cells harboring the expression vehicle can be cultured in conventional nutrient media, adapted as needed for activation of a chosen nucleic acid, repression of a chosen nucleic acid, selection of transformants, or amplification of a chosen nucleic acid.

Expression systems can be selected based on their ability to produce proteins that are modified (e.g., by phosphorylation, glycosylation, or cleavage) in substantially the same way they would be in a cell in which they are naturally expressed. Alternatively, the system can be one in which naturally occurring modifications do not occur, or occur in a different position, or to a different extent, than they otherwise would.

If desired, the host cells can be those of a stably-transfected cell line. Vectors suitable for stable transfection of mammalian cells are available to the public (see, e.g., Pouwels et al. as are methods for constructing them (see, e.g., Ausubel et al.). In one example, a Wnt5a nucleic acid is cloned into an expression vector that includes the dihydrofolate reductase (DHFR) gene. Integration of the plasmid and, therefore, the nucleic acid it contains, into the host cell chromosome is selected for by including 0.01-300 mM methotrexate in the cell culture medium (as described in Ausubel et al., supra). This dominant selection can be accomplished in most cell types.

Moreover, recombinant protein expression can be increased by DHFR-mediated amplification of the transfected gene. Methods for selecting cell lines bearing gene amplifications are described in Ausubel et al. (supra) and generally involve extended culture in medium containing gradually increasing levels of methotrexate. DHFR-containing expression vectors commonly used for this purpose include pCVSEII-DHFR and pAdD26SV(A) (which are also described in Ausubel et al., supra).

A number of other selection systems can be used. These include those based on herpes simplex virus thymidine kinase, hypoxanthine-guanine phosphoribosyl-transferase, and adenine phosphoribosyltransferase genes, which can be employed in tk, hgprt, or aprt cells, respectively. In addition, gpt, which confers resistance to mycophenolic acid (Mulligan et al., *Proc. Natl. Acad. Sci. USA,* 78:2072, 1981); neo, which confers resistance to the aminoglycoside G-418 (Colberre-Garapin et al., *J. Mol. Biol.* 150:1, 1981); and hygro, which confers resistance to hygromycin (Santerre et al., *Gene* 30:147, 1981), can be used.

Wnt5a proteins (and biologically active fragments or other mutants thereof) for use in the methods described herein, and methods to make them, are known in the art. These proteins can be made by, for example, inserting a nucleic acid encoding Wnt5a into an expression vector, transforming cells with the vector, and culturing the cells under conditions that allow the inserted nucleic acid to be expressed. The gene product (protein) can then be purified from the cells or the culture medium in which the cells were grown. The protein can be isolated by affinity chromatography following, optionally, lysis and fractionation of the cells. Where a Wnt5a protein has been fused to a heterologous protein (e.g., a maltose binding protein, a β-galactosidase protein, or a trpE protein), antibodies or other agents that specifically bind to the latter can facilitate purification. The recombinant protein can, if desired, be further purified (e.g., by high performance liquid chromatography or other standard techniques (see, e.g., Fisher, *Laboratory Techniques In Biochemistry And Molecular Biology*, Eds., Work and Burdon, Elsevier, 1980). Biologically active fragments and mutants can also be made using known methods, e.g., random or site-directed mutagenesis, deletions, or other genetic manipulations can be used to make suitable alterations to a sequence encoding a Wnt5a protein, and such mutants can be evaluated for biological activity, e.g., by screening for the effect of the mutant on cell proliferation, cyclin D1 levels, and/or phosphorylation of CamK II, c-Jun, or Dishevelled (dvl) or LEF1.

Other purification schemes are known as well. For example, non-denatured fusion proteins can be purified from human cell lines as described by Janknecht et al. (*Proc. Natl. Acad. Sci. USA,* 88:8972, 1981). In this system, a nucleic acid is subcloned into a vaccinia recombination plasmid such that it is translated, in frame, with a sequence encoding an N-terminal tag consisting of six histidine residues. Extracts of cells infected with the recombinant vaccinia virus are loaded onto $Ni^{2+}$ nitriloacetic acid-agarose columns, and histidine-tagged proteins are selectively eluted with imidazole-containing buffers.

Of course, Wnt5a proteins useful in practicing the methods described herein, particularly fragments of the protein sequence within encoded by the Wnt5a gene, can also be chemically synthesized (e.g., proteins can be synthesized by the methods described in *Solid Phase Peptide Synthesis,* 2nd Ed., The Pierce Chemical Co., Rockford, Ill., 1984).

While the preceding discussion has focused on cell-based expression systems, the invention also features expression vectors that can be transcribed and translated in vitro using, for example, a T7 promoter and T7 polymerase. Thus, the invention encompasses methods of making the proteins described herein in vitro.

Regardless of the manner in which it was made, once sufficiently pure, the proteins can be used as described herein. For example, one can administer the protein to a subject, use it in diagnostic or screening assays, or use it to generate antibodies.

The cells per se can also be administered to subjects in the context of replacement therapies. For example, isolated Wnt5a gene can be operably linked to a promoter, e.g., an inducible promoter (e.g., a steroid hormone receptor-regulated promoter) and introduced into a human or nonhuman (e.g., porcine) cell and then into a subject. Optionally, the cell can be cultivated for a time or encapsulated in a biocompatible material, such as poly-lysine alginate. See, e.g., Lanza, *Nature Biotechnol.* 14:1107, 1996; Joki et al. *Nature Biotechnol.* 19:35, 2001; and U.S. Pat. No. 5,876,742. When a steroid hormone receptor-regulated promoter is used, protein production can be regulated in the subject by administering a steroid hormone to the subject.

In some embodiments, a Wnt5a gene is linked to a native Wnt5a promoter and/or other regulatory sequences and introduced into a cell, e.g., a B cell that has a reduced level of Wnt5a (e.g., due to a mutation or deletion in the Wnt5a gene), that was previously removed from the subject. The cell can be expanded in culture for some time, e.g., before or after the Wnt5a-encoding nucleic acid is introduced into the cell. In some embodiments, the nucleic acid is designed to integrate into the genome of the cell. When the cell is returned to the subject, the cell expresses a statistically normal amount of Wnt5a. Such methods can be used to treat a disease associated with reduced Wnt5a expression, e.g., a hematopoietic malignancy.

While the host cells described above express recombinant proteins, the invention also encompasses cells in which Wnt5a gene expression is disrupted (e.g., cells in which a Wnt5a gene allele has been knocked out, or a gene that regulates Wnt5a expression has been altered, e.g., increased, knocked out, or reduced). These cells can serve as models of disorders that are related to mutated or mis-expressed Wnt5a alleles, e.g., hematopoietic malignancies, e.g., leukemia (e.g., chronic leukemia or acute leukemia, e.g., acute myeloid leukemia or acute lymphoblastic leukemia), lymphoma (e.g., Hodgkin's and non-Hodgkin's Lymphoma, e.g., B cell lymphoma, Burkitt's lymphoma, diffuse cell lymphoma, follicular lymphoma, immunoblastic large cell lymphoma, lymphoblastic lymphoma, mantle cell lymphoma, mycosis fungoides, post-transplantation lymphoproliferative disorder, small non-cleaved cell lymphoma, and T-cell lymphoma), and myeloma, and are also useful in drug screening.

Protein expression can also be regulated in cells without using the genetic constructs described above. Instead, one can modify the expression of an endogenous gene within a cell (e.g., a cell line or microorganism) by inserting a heterologous DNA regulatory element into the genome of the cell such that the element is operably linked to the endogenous gene. For example, an endogenous gene that is "transcriptionally silent," (i.e., not expressed at detectable levels) can be activated by inserting a regulatory element that promotes the expression of a normally expressed gene product in that cell. Techniques such as targeted homologous recombination can be used to insert the heterologous DNA (see, e.g., U.S. Pat. No. 5,272,071 and WO 91/06667).

Pharmaceutical Compositions.

Wnt5a compositions (e.g., compositions comprising Wnt5a nucleic acids and proteins, such as are known in the art, e.g., Genbank Accession Nos. NM_003392 (human nucleic acid), L20861 (human nucleic acid), NP_003383.1 (human protein), AAA16842.1 (human protein), BC018425 (mouse nucleic acid), NM_009524 (mouse nucleic acid), AAH18425 (mouse protein), NP_033550.1 (mouse protein)) fragments thereof, hybrid sequences of which they are a part, and gene constructs containing the Wnt5a gene; proteins, including protein encoded by the Wnt5a gene, fragments thereof, chimeras, and antibodies that specifically bind thereto; and cells, including those that are engineered to express the nucleic acids or proteins described herein) can be incorporated into pharmaceutical compositions, and administered to a subject in methods for the treatment of diseases associated with reduced Wnt5a levels, e.g., hematopoietic malignancies such as leukemia (e.g., chronic leukemia or acute leukemia, e.g., acute myeloid leukemia or acute lymphoblastic leukemia), lymphoma (e.g., Hodgkin's and non-Hodgkin's Lymphoma, e.g., B cell lymphoma, Burkitt's lymphoma, diffuse cell lymphoma, follicular lymphoma, immunoblastic large cell lymphoma, lymphoblastic lymphoma, mantle cell lymphoma, mycosis fungoides, post-transplantation lymphoproliferative disorder, small non-cleaved cell lymphoma, and T-cell lymphoma), and myeloma. These compositions typically also include a solvent, a dispersion medium, a coating, an antimicrobial (e.g., an antibacterial or antifungal) agent, an absorption delaying agent (when desired, such as aluminum monostearate and gelatin), or the like, compatible with pharmaceutical administration (see below). Active compounds, in addition to those of the present invention, can also be included in the composition and may enhance or supplement the activity of the present agents.

The composition will be formulated in accordance with their intended route of administration. Acceptable routes include oral or parenteral routes (e.g., intravenous, intradermal, transdermal (e.g., subcutaneous or topical), or transmucosal (i.e., across a membrane that lines the respiratory or anogenital tract). The compositions can be formulated as a solution or suspension and, thus, can include a sterile diluent (e.g., water, saline solution, a fixed oil, polyethylene glycol, glycerine, propylene glycol or another synthetic solvent); an antimicrobial agent (e.g., benzyl alcohol or methyl parabens; chlorobutanol, phenol, ascorbic acid, thimerosal, and the like); an antioxidant (e.g., ascorbic acid or sodium bisulfite); a chelating agent (e.g., ethylenediaminetetraacetic acid); or a buffer (e.g., an acetate-, citrate-, or phosphate-based buffer). When necessary, the pH of the solution or suspension can be adjusted with an acid (e.g., hydrochloric acid) or a base (e.g., sodium hydroxide). Proper fluidity (which can ease passage through a needle) can be maintained by a coating such as lecithin, by maintaining the required particle size (in the case of a dispersion), or by the use of surfactants.

The Wnt5a compositions described herein can be prepared as sterile powders (by, e.g., vacuum drying or freeze-drying), which can contain the active ingredient plus any additional desired ingredient from a previously sterile-filtered solution.

Oral compositions generally include an inert diluent or an edible carrier. For example, the active compound can be incorporated with excipients and used in the form of tablets, troches, or capsules (e.g., gelatin capsules). Oral compositions can be prepared using fluid carries and used as mouthwashes. The tablets etc. can also contain a binder (e.g., microcrystalline cellulose, gum tragacanth, or gelatin); an excipient (e.g., starch or lactose), a disintegrating agent (e.g., alginic acid, Primogel, or corn starch); a lubricant (e.g., magnesium stearate or Sterotes); a glidant (e.g., colloidal silicon dioxide); a sweetening agent (e.g., sucrose or saccharine); or a flavoring agent (e.g., peppermint, methyl salicylate, or orange flavoring).

For administration by way of the respiratory system, the compositions can be formulated as aerosol sprays (e.g., from a pressured container or dispenser that contains a suitable propellant (e.g., a gas such as carbon dioxide), or a nebulizer. The ability of a composition to cross a biological barrier can be enhanced by agents known in the art. For example, detergents, bile salts, and fusidic acid derivatives can facilitate transport across the mucosa (and therefore, be included in nasal sprays or suppositories).

For topical administration, the active compounds are formulated into ointments, salves, gels, or creams according to methods known in the art.

Controlled release can also be achieved by using implants and microencapsulated delivery systems (see, e.g., the materials commercially available from Alza Corporation and Nova Pharmaceuticals, Inc.; see also U.S. Pat. No. 4,522,811 for the use of liposome-based suspensions).

The Wnt5a pharmaceutical compositions described herein can be formulated in dosage units (i.e., physically discrete units containing a predetermined quantity of the active compound) for uniformity and ease of administration.

The toxicity and therapeutic efficacy of any given compound can be determined by standard pharmaceutical procedures carried out in cell culture or in experimental animals. For example, one of ordinary skill in the art can routinely determine the LD50 (the dose lethal to 50% of the population) and the ED50 (the dose therapeutically effective in 50% of the population). The dose ratio between toxic and therapeutic effects is the therapeutic index. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used to formulate a range of dosage for use in humans (preferably a dosage within a range of circulating concentrations that include the ED50 with little or no toxicity). The dosage may vary within this range depending upon the formulation and the route of administration. For any compound used in the method described herein, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

A therapeutically effective amount of a Wnt5a protein described herein can range from about 0.001 to 30 mg/kg body weight (e.g., about 0.01 to 25 mg/kg, about 0.1 to 20 mg/kg, or about 1 to 10 (e.g., 2-9, 3-8, 4-7, or 5-6) mg/kg). The protein can be administered one time per week for between about 1 to 10 weeks (e.g., 2 to 8 weeks, 3 to 7 weeks, or about 4, 5, or 6 weeks). However, a single administration can also be efficacious. Certain factors can influence the dosage and timing required to effectively treat a subject. These factors include the severity of the disease, previous treatments, and the general health or age of the subject.

As noted above, the present invention encompasses agents (e.g., small molecules, antibodies, proteins, nucleic acids) that modulate (e.g., increase) expression or activity of the Wnt5a gene or the protein encoded by the Wnt5a gene. Exemplary doses of these agents include milligram or microgram amounts of the small molecule per kilogram of subject or sample weight (e.g., about 1-500 mg/kg; about 100 mg/kg; about 5 mg/kg; about 1 mg/kg; or about 50 µg/kg). Appropriate doses of a small molecule depend upon the potency of the small molecule with respect to the expression or activity to be modulated. When one or more of these small molecules is to be administered to an animal (e.g., a human) to modulate expression or activity of nucleic acid or protein described herein, a physician, veterinarian, or researcher may prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The Wnt5a nucleic acid molecules described herein can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al, *Proc. Natl. Acad. Sci. USA* 91:3054-3057, 1994). The pharmaceutical preparation of the gene therapy vector can include the gene therapy vector in an acceptable diluent, or can comprise a slow release matrix in which the gene delivery vehicle is imbedded. Wnt5a-expressing gene therapy vectors can be mixed with liposomes or liposomal complexes according to methods known in the art prior to administration to cells in culture or in vivo. Alternatively, where the complete gene delivery vector can be produced intact from recombinant cells (e.g. retroviral vectors), the pharmaceutical preparation can include one or more cells which produce the gene delivery system. The Wnt5a pharmaceutical compositions described herein can be included in a container, pack, or dispenser together with instructions for administration.

Cell-Based Methods of Treatment

As described herein, loss of Wnt5a was seen in cells from human subjects with acute lymphoblastic leukemia and acute myeloid leukemia. Such subjects can be treated by cell-based methods. For example, the methods can include removing a cell from the subject, e.g., a blood cell such as a B cell or a hematopoietic stem cell, transducing the cell with a nucleic acid encoding a Wnt5a polypeptide or active fragment thereof, culturing the cell under conditions such that the Wnt5a polypeptide is expressed, and returning the cell to the subject. In some embodiments, the Wnt5a nucleic acid integrates into the genome of the cell. General methods for removing and purifying selected cells, preparing the nucleic acid encoding a Wnt5a polypeptide, culturing the cells, and returning the cell to the subject are all known in the art, and suitable general clinical methodology is described in, e.g., Cavazzana-Calvo et al., Science. 2000 288(5466):669-72; Vereecque et al., J Gene Med. 2003 October; 5(10):852-9; Bai et al., Gene Ther. 2003 10(17):1446-57; Schmidt-Wolf and Schmidt-Wolf, Clin Exp Med. 2003 3(1):4-14. The methods can be used in conjunction with standard treatments, e.g., radiation and/or chemotherapeutic methods.

The invention is further described in the following examples, which do not limit the scope of the invention described in the claims.

EXAMPLES

Example 1

Wnt5a Functions as a Tumor Suppressor in Mice

The present inventors demonstrated that Wnt5a-null mice die at birth and exhibit multiple developmental defects, whereas Wnt5a-heterozygous mice are viable, fertile and appear normal (Yamaguchi, et al., *Development* 126:1211-23, 1999). Surprisingly, some of the Wn5a+/− mice develop B cell lymphomas as early as 16 weeks of age; thus, the role of Wnt5a in B cell proliferation and differentiation was examined.

RT-PCR was utilized to determine the pattern of Wnt5a expression in a variety of mouse hematopoietic tissues.

Analysis of RNA by RT-PCR and Southern blots. Total RNA was prepared using TRIzol (Invitrogen). An assay combining reverse transcription with polymerase chain reaction (an RT-PCR assay) was carried out using SuperScript One-Step RT-PCR with Platinum Taq kit (Invitrogen). Primer pairs (from 5' to 3') are: (1) for human Wnt5a, ctacgagagtgctcg-catcctcatg (forward; SEQ ID NO: 1) and cattgcgcacgcagtagt-cag (reverse SEQ ID NO:2); (2) for mouse Wnt5a, tcgggactg-gttgtgggg (forward; SEQ ID NO:3) and agctcgcagccgtccatc (reverse; SEQ ID NO:4); (3) for human GAPDH, cagcctcaa-gatcatcagca (forward; SEQ ID NO:5) and tgagcttgacaaagtg-gtcg (reverse; SEQ ID NO:6); and (4) for mouse GAPDH, caccatggagaaggccgggg (forward; SEQ ID NO:7) and gacg-gacacattggggtag (reverse; SEQ ID NO:8). The RT-PCR cycling parameters are: 48° C. for 30 seconds; 94° C. for 2 minutes; 26 cycles (for GAPDH) or 42 cycles (for human and mouse Wnt5a) at 94° C. for 30 seconds, 55° C. (for human WNT5A), or 60° C. (for mouse Wnt5a and GAPDH of both mouse and human) for 30 seconds and 72° C. for 1 minute with a final extension of 72° C. for 10 minutes after the last cycle. Following RT-PCR and gel electrophoresis, Southern analysis was performed to confirm the identity of the Wnt5a PCR fragments.

Figure 2:
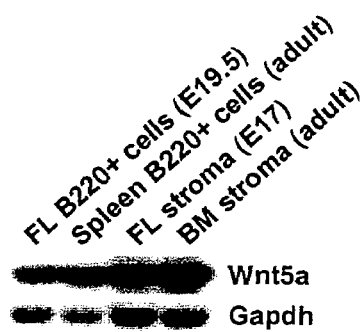
FIG. 2 is a representation of an autoradiogram depicting Wnt5a and gapdh (a positive control) expression in hematopoietic tissues and cells (left to right-hand lanes: FL (fetal liver) B220+ cells (at E19.5), spleen B220+ cells (adult), FL stroma (E17), and BM stroma (adult)) following amplification by RT-PCR.
Figure 3:
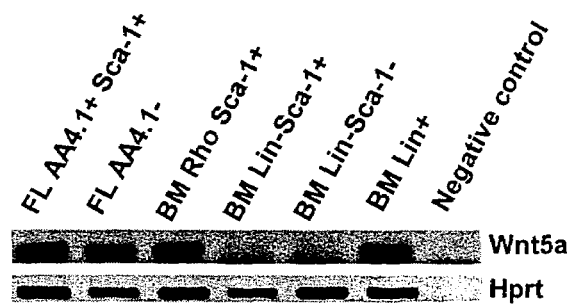
FIG. 3 is a representation of an autoradiogram depicting expression of Wnt5a and hprt (a positive control) in mouse hematopoietic progenitor cells and mature cells (left to right-hand lanes: FL AA4.1+Sca-1+, FL AA4.1−, BM Rho Sca-1+, BM Lin-Sca-1+, BM Lin-Sca-1−, BM Lin+, and negative control).

Wnt5a is expressed in splenic B cells, fetal liver B cell progenitors, and in cultured primary murine fetal liver and bone marrow stromal cells (FIG. 2). Cells prepared from E17 fetal liver (FL) of wild-type and Wnt5a null mice and from 6 week old wild-type mouse bone marrow were cultured as described previously (Whitlock et al., *J. Immunol. Methods* 67:353-369, 1984). During fetal hematopoiesis, Wnt5a is transcribed in cell populations enriched for fetal liver hematopoietic stem cells (HSC) (Sca-1$^+$c-kit$^+$AA4.1$^+$Lin$^-$ cells) and progenitor cells (AA4.1$^-$cells). (FIG. 3). Wnt5a is also expressed in adult bone marrow (BM) HSC (Rho-123low/Sca-1+/c-kit+/Lin−) that is highly enriched for HSC activity. Interestingly, Wnt5a transcripts are not observed in more heterogeneous populations of HSC (Lin$^-$Sca-1$^+$ BM cells, representing 0.1-0.2% of normal BM cells) or progenitors (Lin$^-$Sca-1$^-$ cells). Wnt5a expression is upregulated in committed progenitors and mature blood cell types (Lin+bone marrow cells) (Jurecic et al., *Blood* 82:2673-2683, 1993; Li and Johnson, *Blood* 85:1472-1479, 1995; Jordan et al., *Exp. Hematol.* 23:1011-1015, 1995; Phillips et al., *Science* 288:1635-1640, 2000).

Figure 4:
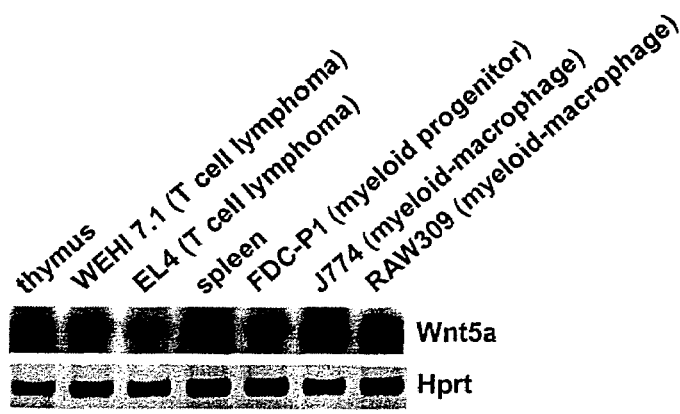
FIG. 4 is a representation of an autoradiogram depicting expression of Wnt5a and hprt in hematopoietic cell lines and tissues (left to right-hand lanes: thymus, WHI 7.1 (T cell lymphoma), EL4 (T cell lymphoma), spleen, FDC-P1 (myeloid progenitor), J774 (myeloid-macrophage), and RAW309 (myeloid-macrophage).

Analysis of a panel of mouse lineage-specific hematopoietic cell lines demonstrates that Wnt5a is ubiquitously expressed in different stages of B cell, T cell, and myeloid cell development (FIG. 4). These results demonstrate that Wnt5a is widely expressed in several hematopoietic lineages and tissues.

Example 2

Absence of Wnt5a Increases B Cell Proliferation in a Cell Autonomous Manner

Due to the perinatal lethality of Wnt5a-null mice, examination of the Wnt5a effects on B cells was restricted to fetal liver (FL), which supports B cell development from embryonic day 13 (E13) to birth. In order to maintain an inbred genetic background in these studies, we bred germline-transmitting Wnt5a chimeric mice to $129Sv^{Brd}$ mice to establish 129-strain mice bearing the Wnt5a-null allele. These animals are within the scope of the present invention. Embryos were harvested from intercrosses of these Wnt5a-heterozygous mice, and Wnt5a-null mice were initially identified by morphology. The genotypes of all samples were subsequently confirmed by PCR. E19 FL cells were isolated and stained with anti-B220 antibody, a B cell surface marker, and analyzed by flow cytometry. Single-cell suspensions were prepared from E19 FL and stained with anti-B220-APC (Caltag Laboratory), -CD43-PE (PharMingen) IgM-FITC (PharMingen). The analysis was performed with FACSCalibur flow cytometer (Becton Dickinson) and FlowJo software (Tree Star, Inc).

Figure 5A:
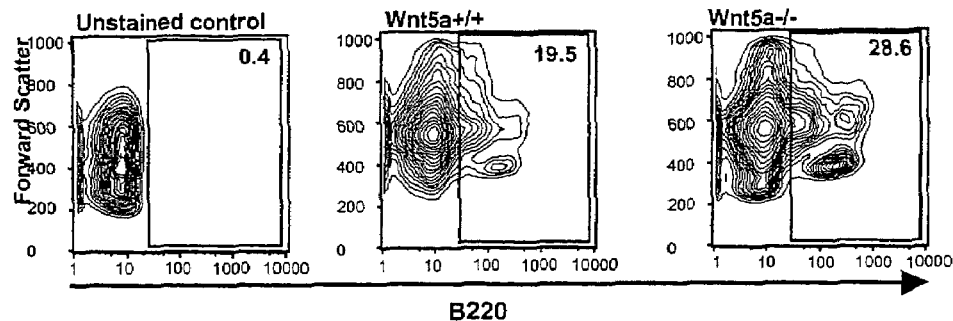
FIGS. 5A-5C are three graphs depicting expansion and hyperproliferation of B lymphocytes in Wnt5a-null mice. Flow cytometry analysis was performed on unstained control cells (left-hand graphs), antibody-bound Wnt5a+/+ cells (middle graphs) and antibody-bound stained Wnt5a−/− FL cells (right-hand graphs). Antibodies used were anti-B220 (5A), anti-CD43 (5B) and anti-IgM control (5C).

Wnt5a-null mice display a 35% increase in the proportion of B-lineage cells (FIG. 5A) and a 55% increase in the absolute number of B cells. To determine whether an absence of Wnt5a alters B cell differentiation, we stained various populations with combinations of antibodies against B220, CD43, and IgM. The results are summarized in Table 1.

TABLE 1

Percentage of B cells in E19 fetal liver

|  | Pro-B cells (%) (B220+ & CD43+) | Pre-B cells (%) (B220+ & CD43−) | Immature B cells (%) (IgM) |
| --- | --- | --- | --- |
| WNT5A+/+ FL | 16.4 ± 1.9 | 2.33 ± 0.19 | 18 ± 5 |
| Wnt5a−/− FL | 20.5 ± 0.1 | 5.1 ± 0.6 | 30 ± 1.6 |

Figure 5B:
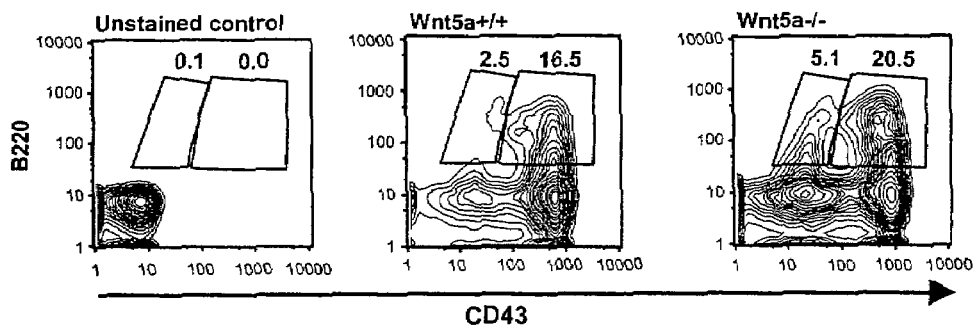
Figure 5C:
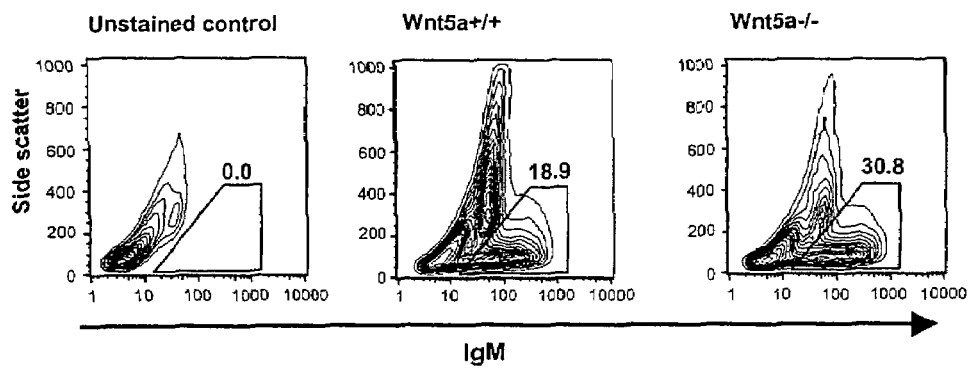

As shown, there was an increase in the number of pro-B cells (B220+/CD43+) and pre-B cells (B220+/CD43−) in Wnt5a-null FL (FIG. 5B). Because immature B cells (IgM+) are very rare in wild-type E19 fetal liver, the differentiation of Wnt5a-null FL into immature B cells by in vitro culture was assessed. After 8 days in culture, Wnt5a-null FL produced 166% (about 1.7 times) as many IgM+, immature B cells as wildtype FL (FIG. 5C). Thus, an absence of Wnt5a does not block B cell development from pro-B to immature B stage in fetal liver.

Interestingly, while 20% more pro-B cells were present in Wnt5a-null FL than in wild-type FL, the increase in pre-B cell and immature B cell numbers in the Wnt5a-null FL was more striking.

Figure 6:
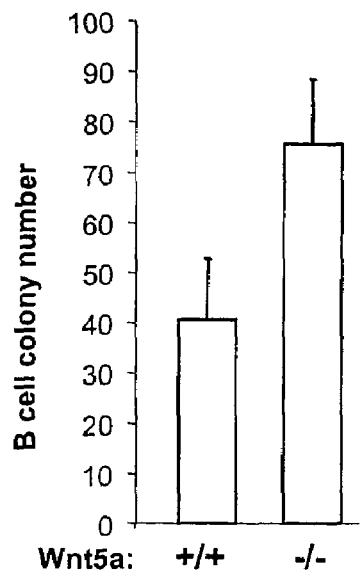
FIG. 6. is a bar graph depicting expansion and hyperproliferation of B lymphocytes in Wnt5a-null mice. The bars indicate the number of colonies formed per $10^5$ cells following a methylcellulose colony-forming assay (+/+ indicates wild-type cells and –/– indicates Wnt5a-null FL cells).

To confirm the increase in progenitor B cells in Wnt5a-null FL, colony forming assays were performed using FL cells harvested from wildtype or Wnt5a-null embryos at E19. Cells were prepared from E19.5 Wnt5a+/+ and −/− FL and $9\times10^4$ cells were plated in methylcellulose media M3630 supplemented with IL-7, according to the manufacturer's instructions (StemCell Technologies). Colonies (>50 cells) were counted seven days later using an inverted microscope at 40× magnification. Approximately 90% more colonies were detected with Wnt5a-null FL than with wild-type FL when grown in methylcellulose cultures supplemented with IL-7, which facilitates growth of pro-B and pre-B cell colonies (StemCell Technologies) (FIG. 6). In addition to forming more colonies, FL cells from Wnt5a-null mice also formed larger-sized colonies, suggesting that Wnt5a-null B cells proliferate faster than wild-type B cells in these assays.

Example 3

Wnt5a Signals Via the Wnt/Ca$^{++}$ Pathway to Modulate B Cell Proliferation

Figure 10:
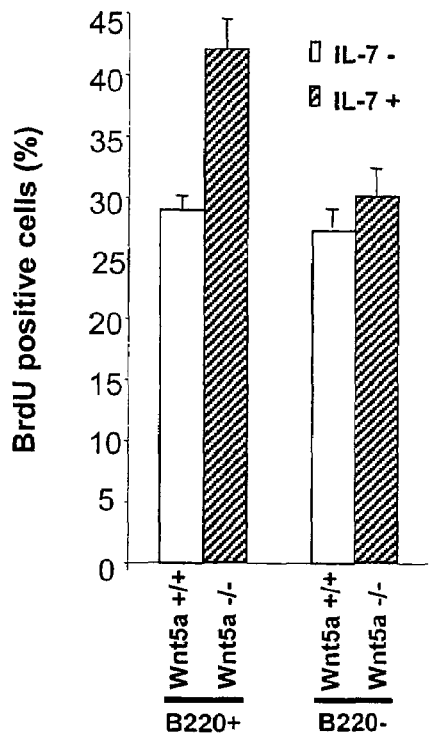
FIG. 10 is a bar graph depicting expansion and hyperproliferation of B lymphocytes (BrdU positive cells (%)) in wild type and Wnt5a null mice. B220-positive and B220-negative FL cells, labeled in vivo with BrdU, were stained with anti-BrdU-FITC and analyzed by flow cytometry.

To determine if the augmented B cell numbers in Wnt5a-null FL are due to higher rates of cell proliferation or due to increased resistance of Wnt5a-null cells to apoptosis. BrdU incorporation assays and TUNEL (terminal deoxynuclotidyl transferase-mediated dUTP nick end-labeling) assays were performed on FL cells (FIG. 10). Mice were injected intraperitoneally with 50 µg BrdU/gram body weight on the $18^{th}$ day of pregnancy. Embryos were harvested one hour after injection, and the fetal liver removed and stained with anti-B220-APC and sorted. Cells were subsequently stained with anti-BrdU-FITC (Becton Dickson) according to supplier's instruction and analyzed by flow cytometry, as above.

The Wnt5a-null mice contain 50% more BrdU positive, B220+ cells than wild-type mice, indicating that Wnt5a negatively regulates B cell proliferation. The difference is less profound in the B220-negative population. No difference was found in the number of TUNEL positive cells in E19 wildtype and Wnt5a mutant B220+ cells. Taken together, these results indicate that the increase of the B-lineage cell compartment in Wnt5a-null FL results from increased proliferation of B cells and not from alteration in the resistance of B cells to apoptosis.

Example 4

Wnt5a Inhibits B Cell Proliferation in a Cell-Autonomous Manner

To determine whether Wnt5a inhibits B cell proliferation in a cell-autonomous manner, we performed adoptive transfer experiments.

Rag1−/− mice (C57BL/6 strain, from Jackson Laboratory) were used as recipients and received 900 cGy 467g468-irradiation (137Cs source, dose rate 81cGy/min) four hours before cell transfer. $5\times10^6$ wildtype or Wnt5a null FL cells prepared from E16 FL were transplanted by intravenous injection into the lethally irradiated Rag1−/− mice. Six week post-transplant, bone marrow, spleen and peripheral blood cells were harvested and examined by flow-cytometry. Both the percentage and the absolute numbers of pro-B (B220+/CD43+), pre-B (B220+/CD43−/IgM−), IgM+B cells (B220+/IgM+) in bone marrow, and mature follicular B cells (IgM$^{low}$/IgD$^{high}$) in the spleen were greater in mice transplanted with Wnt5a-null FL cells than those rescued with wildtype FL (FIG. 17A-F; FIG. 18). Increased numbers of mature follicular B cells (IgM$^{low}$/IgD$^{high}$) were also observed in the peripheral blood of recipients transplanted with Wnt5a-null FL (data not shown). These findings indicate that the increased rate of B cell proliferation observed in Wnt5a-deficient mice is due to loss of a cell-intrinsic signal that cannot be complemented by physiologic levels of Wnt5a present in serum or in the stroma.

Example 5

Wnt5a Inhibits the Response of B cells to IL-7

Figure 11:
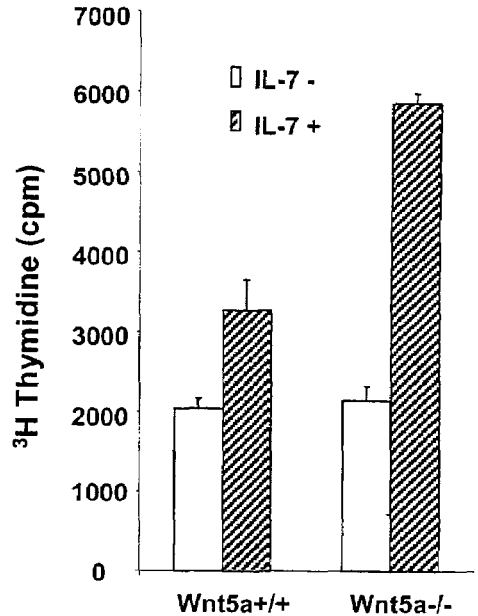
FIG. 11 is a bar graph depicting expansion and hyperproliferation of B lymphocytes from fetal liver in wildtype and Wnt5a-null mice. Proliferation was measured by the uptake of tritiated thymidine ($^3$H thymidine (cpm)) in cultured-B220 positive cells, sorted from wild-type and Wnt5a-null mice, in the presence (filled bars) or the absence (open bars) of IL-7.

B cells are critically dependent on the cytokine interleukin-7 (IL-7) for growth (Fry & Mackall. *Blood* 99:3892-904, 2002) and the increase in Wnt5a-null B cell numbers and size of the colonies observed in the colony-forming assays suggests that hyperproliferation in the absence of Wnt5a could result from alterations in the responsiveness of the B cells to IL-7. To test this possibility, assays with [$^3$H] thymidine were performed on FACS-sorted FL B cells cultured in the presence or absence of IL-7 (FIG. 11). Sorted B220-positive cells ($2 \times 10^5$) were plated into wells of 96-well plates with 200 μl of RPMI supplemented with 5% FCS, 2 mM L-glutamine, 100 μg/ml streptomycin, 100 U/ml penicillin, and 50 μM 2-mercaptoethanol (GIBCO-BRL) in the presence or absence of IL-7 (0.5 ng/ml, StemCell Technologies). After 48 hours of culture at 37° C. with 10% $CO_2$, cells were pulsed with [$^3$H] thymidine (1 μCi per well) for 16 hours before being harvested. Incorporated radioactivity was quantified with a Liquid Scintillation and Luminescence Counter (Perkin Elmer Wallac Inc).

Figure 12:
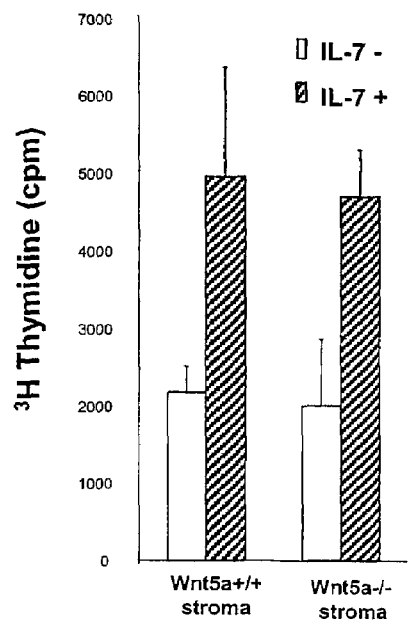
FIG. 12 is a bar graph depicting expansion and hyperproliferation of B lymphocytes from Wnt5a null FL B220+ cells cultured on stromal layers derived from wildtype or Wnt5a null FL (3H thymidine (cpm)). Thymidine uptake of FL B220+ cells was adjusted by subtracting the tritiated thymidine uptake by stromal cells.

Wildtype and mutant B cells have similar [$^3$H] thymidine uptake in the absence of IL-7. However, Wnt5a-null B cells display an increased rate of [$^3$H] thymidine uptake in the presence of IL-7 relative to wild-type samples, suggesting that Wnt5a alters the responsiveness of B cells to IL-7. The proliferation rate of Wnt5a-null B220+ cells when cultured on stromal cell feeder layers derived from either wildtype FL or Wnt5a-null FL cells was also assessed. There was no difference in the response of Wnt5a null FL cells to IL-7 stimulation when the cells were grown on stromal cell feeder layers derived from either wild-type FL or Wnt5a-null FL (FIG. 12). The inability of the wildtype stromal cells to compensate for the dysfunction of Wnt5a in the B cells indicates that Wnt5a-mediated suppression of IL-7 stimulation is cell autonomous, consistent with the results of the FL adoptive transfer experiment described herein.

To analyze the effect of Wnt5a on apoptosis, TUNEL (terminal deoxynuclotidyl transferase-mediated dUTP nick end-labeling) assays were performed on wildtype and Wnt5a-null FL cells. No difference was found in the number of TUNEL positive cells in E19 wildtype and mutant B220-positive cells. These results indicate that the increase of the B-lineage cell compartment in Wnt5a-null FL results from increased proliferation of B cells and not from an alteration in the resistance of FL cells to apoptosis.

Example 6

Figure 19:
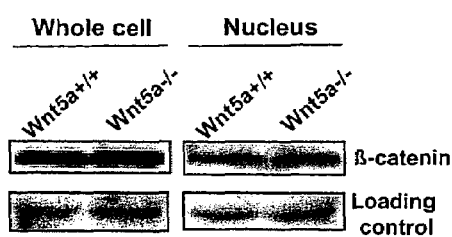
FIG. 19 is a representation of Western blot analysis of E19 FL cells to detect β-catenin protein levels in whole cell (left panels) and nuclear (right panels) extracts from wild type (Wnt5a+/+) FL or Wnt5a null (Wnt5a–/–) FL cells. Antibodies against mouse β-tubulin and Ini1 were used as protein loading controls for whole cell and nuclear extracts, respectively.

Wnt5a Signals Through the Non-Canonical Wnt/Ca++ Pathway and Downregulates Cyclin D1 Expression To dissect the mechanistic pathway utilized by Wnt5a in regulating B cell proliferation, β-catenin levels in wildtype and Wnt5a-null FL were analyzed. Cells were lysed with 1% NP40, 0.5% sodium deoxylate, 0.1% SDS and protease inhibitor cocktail tables (Complete) in PBS. Proteins were separated by 10% SDS-polyacrylamide gel electrophoresis and transferred to nitrocellulose membrane (BIO-RAD). Immunoblots were probed with primary antibodies against β-catenin-Exon 3 (Calbiochem), then with anti-IgG-HRP antibodies and visualized using ECL (Amersham Pharmacia Biotech) according to the supplier's instructions. No difference was detected in β-catenin levels in whole cell or in nuclear extracts between the two genotypes, suggesting that Wnt5a was neither activating nor inhibiting the canonical, Wnt/β-catenin pathway in FL (FIG. 19). Therefore, the Wnt/Ca++ pathway was examined.

Figure 13:
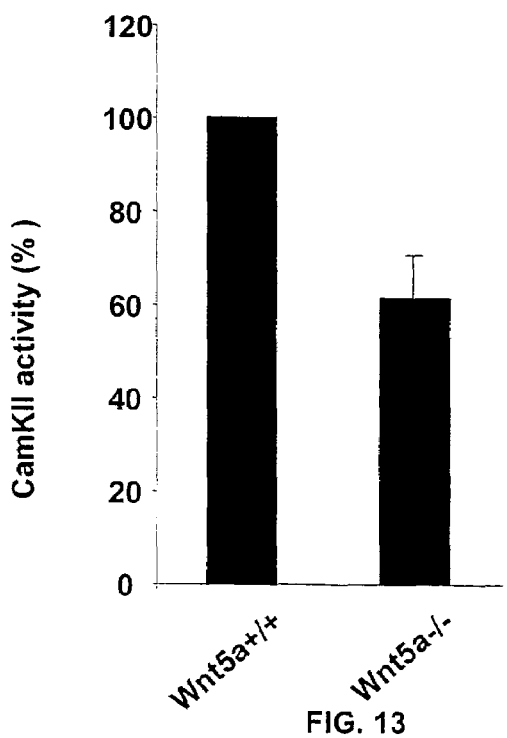
FIG. 13 is a bar graph depicting CamK II activity (%) in Wnt5a+/+ and Wnt5a–/– cells. Wildtype FL CamK II activity is presented as 100% and mutant FL is shown as a percentage of wildtype activity.

CamK II activity was analyzed in Wnt5a wild-type and null FL cells (FIG. 13). Fetal liver was lysed in 50 mM Hepes, 270 mM KCl, 0.1 mM. EDTA, 0.1 mM EGTA, 10% glycerol and 1% NP40. Cytoplasmic protein was recovered by centrifugation and concentrations determined by BCA Protein (Pierce). CamK II activity was measured using a CaM Kinase II Assay Kit (Upstate) and 100 μg protein extract according to the supplier's instruction. Incorporated radioactivity was monitored with a Multi-Purpose Scintillation Counter (Beckman Instruments, Inc), and total Cam KII protein levels were determined using an antibody against CamK II (Santa Cruz).

Figure 14:
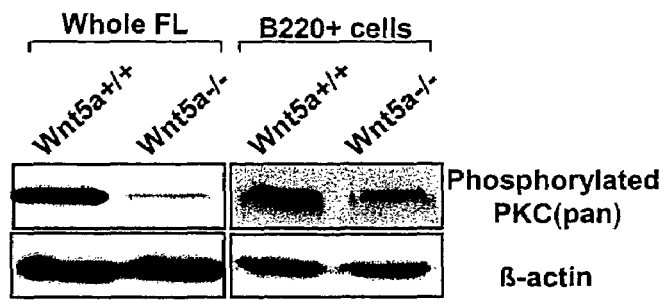
FIG. 14 is a set of four representations of Western blot analysis of whole E19 FL cells (left panels) and B220+ cells (right panels) from Wnt5a+/+ or Wnt5a–/– mice to detect phosphorylated PKC (Pan) (top row). The blot was also stained with anti-β-actin antibodies to verify equal loading (bottom row).

Although immunoblotting revealed equal amounts of CamK II in both samples, Wnt5a-null FL cells possess 40% less CamK II activity than wild-type FL cells. Immunoblotting with antibodies against phosphorylated PKC revealed a reduction in the levels of activated PKC in both Wnt5a-null FL and in Wnt5a-null B220+ cells sorted from E18 FL (FIG. 14).

Figure 20:
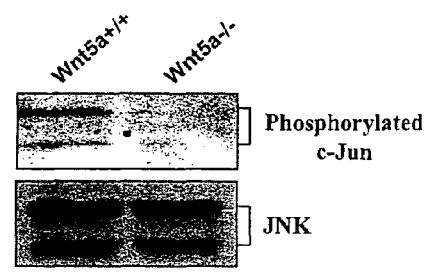
FIG. 20 is a representation of the results of immunoprecipitation analysis of JNK kinase activity, using immunoprecipitates of JNK. The immunocomplexes were assayed for JNK activity using an antibody against phosphorylated c-jun (top panel). Total JNK was detected by Western blot analysis using anti-JNK antibodies (bottom panel).
Figure 21:
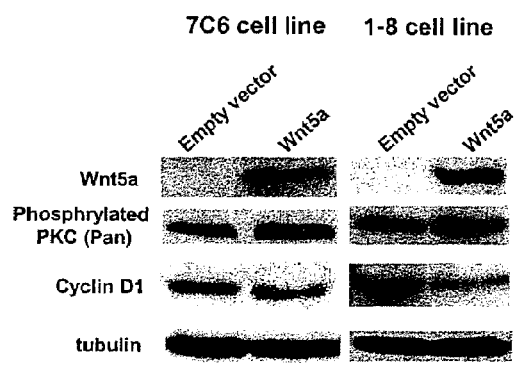
FIG. 21 is a set of eight representations of Western blot analysis of levels of Wnt5a (top row), phosphorylated PKC (pan) (second row), Cyclin D1 (third row) and tubulin (bottom row) after transduction of Wnt5a into 7C6 (left panels) or 1-8 (right panels) mouse B cell lines.

In addition, PKC has been found to activate the c-jun amino-terminal kinase (JNK). (Mitsutake et al., 2001 Oncogene 20, 989-96; Saneyoshi et al., 2002 Nature 417, 295-9). JNK kinase assays were performed using immunoprecipitates of JNK as previously described (Raingeaud et al., 1995 J Biol Chem 270, 7420-6), with phosphorylation of c-Jun detected using phospho-c-Jun antibody (Ser63) (Cell Signalling Technology). Although total JNK levels were equal in Wnt5a-wildtype and null fetal liver, activated JNK was decreased in the absence of Wnt5a (FIG. 20), further suggesting that absence of Wnt5a leads to a reduction in PKC activity. These results indicate that Wnt5a is signalling via the Wnt/Ca$^{++}$ pathway to activate CamK II and PKC.

Figure 16A:
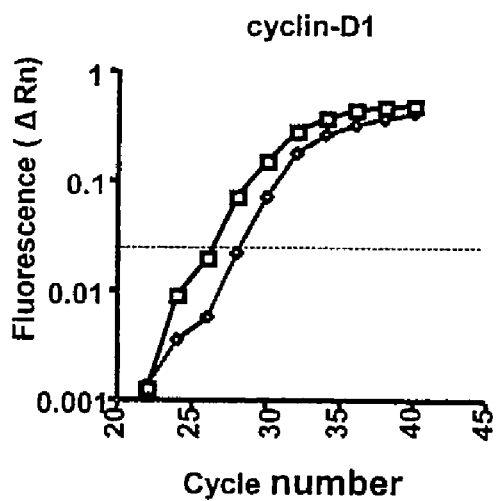
FIGS. 16A-16C are three graphs depicting the results of real time PCR analysis of cyclin D-1 (16A) or c-myc (16B) levels in total RNA extracted from E19.5 wildtype (open diamonds) or Wnt5a-null (open squares) FL cells. The threshold cycle number (CT) for each sample was calculated with a fluorescence threshold (Rn) of 0.3 (indicated by the dashed line). A control real-time PCR experiment using cyclin D1 cDNA as a standard is shown in 16B.

Cyclin-D1 and c-myc are cell cycle regulatory genes whose expression was previously reported to be upregulated in response to Wnt1-mediated activation of the β-catenin pathway. (Rimerman et al, *J. Biol. Chem.* 275:14736-14742, 2000; Willert et al., *BMC Dev. Biol.* 2:8, 2002). The effect of Wnt5a upon regulation of these two genes was examined using real time PCR (FIG. 16A). Relative quantities of mRNA expression were analyzed using QRT-PCR (Applied Biosystems ABI Prism 7700 Sequence Detection System, Applied Biosystems). One-step QRT-PCR reactions were performed in the presence of SYBR green. The primer sequences (5' to 3') were as follows: for mouse cyclin D1, gcgtaccctgacaccaatct (forward; SEQ ID NO:9) and cacaact-tctcggcagtcaa (reverse; SEQ ID NO:10); for mouse c-myc, tgcgacgaggaagagaattt (forward; SEQ ID NO:11) and aac-cgctccacatacagtcc (reverse; SEQ ID NO:12); human cyclin D1 cccgcacgatttcattgaac (forward; SEQ ID NO:13), gcggat-tggaaatgaacttcac (reverse; SEQ ID NO:14). The PCR cycling parameters were the same as used in the RT-PCR described previously. The specificity of amplification was confirmed by electrophoresis of the products on agarose gels.

The threshold cycle numbers (CT) for cyclin D1 in wild-type FL was 28.5 versus 26.8 for Wnt5-null FL. Control experiments utilizing Cyclin D1 cDNA as input template confirmed that a 2-cycle difference in threshold values equates to a four-fold difference in template concentration, indicating that cyclin D1 expression in Wnt5-null FL was increased 4-fold relative to wild-type levels. The CT for c-myc in Wnt5a+/+ and Wnt5a−/− were 26.3 and 26.5 respectively, suggesting no significant difference in c-myc expression levels in the presence or absence of Wnt5a. These results reveal that Wnt5a signals via the Wnt/Ca$^{++}$ pathway to inhibit B cell proliferation and to negatively regulate cyclin D1 levels.

To further confirm the ability of Wnt5a to downregulate Cyclin D1 and inhibit cell proliferation, Wnt5a was transduced into two independent mouse B cell lines.

7C6 cells and 1-8 mouse B cell lines are Abelson leukemia virus-transformed B cells lines that lack Wnt5a expression. The 7C6 and 1-8 B cell lines were cultured in RPMI supplemented with 10% FCS, 2 mM L-glutamine, 100 µg/ml streptomycin, 100 U/ml penicillin, and 50 µM 2-mercaptoethanol (GIBCO-BRL). cells were sorted by FACS. Mouse Wnt5a cDNA was cloned into an MSCV2.2IRES-GFP vector, and MSC-Wnt5a-GFP or MSC-GFP (empty vector) DNA was electroporated into 7C6 cells and 1-8 cells using a Gene Pulser II (BioRad) electroporator at 275 V, 950 mF. GFP-positive transduced cells were harvested by FACS at 48 to 72 hours post-electroporation, and analyzed for proliferation by as propidium iodide and BrdU staining and for expression of Wnt5a and Cyclin D1 by western blot analysis.

Figure 16B:
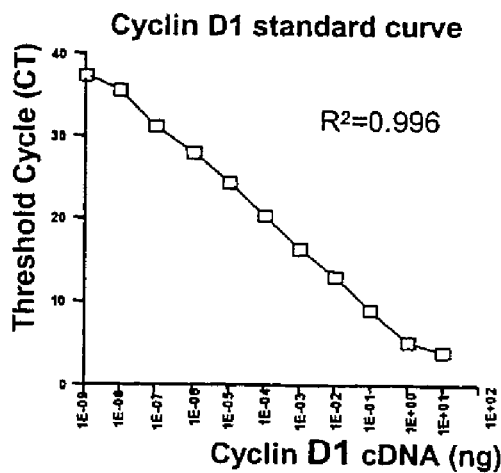
Figure 16C:
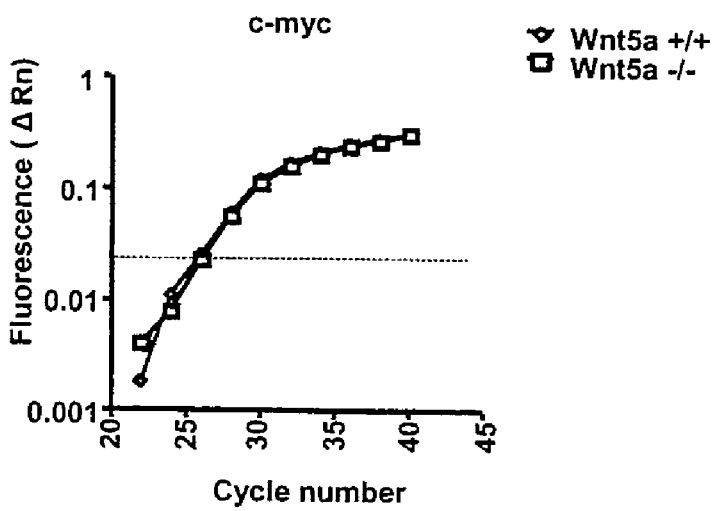

Transduction of Wnt5a into 7C6 or 1-8 cells increased the level of phosphorylated PKC and decreased Cyclin D1 levels, indicating that Wnt5a expression activates the non-canonical signalling pathway and inhibits Cyclin D1 (FIG. 16B). BrdU staining of the transduced cells revealed that expression of Wnt5a reduced proliferation in both B cell lines (FIG. 16C). These data are consistent with the in vivo results described herein indicating that Wnt5a negatively regulates B cell proliferation in a cell autonomous manner by activating the Wnt/Ca$^{++}$ pathway and inhibiting Cyclin D1 expression.

Example 9

Wnt5a Heterozygous Mice Develop B Cell Lymphoma and Chronic Myeloid Leukemia with Loss of Heterozygosity for Wnt5a Function To explore the role of Wnt5a in tumorigenesis, we performed tumor assays on cohorts of Wnt5a heterozygous mice and on genetically matched, wild-type controls. Cohorts of Wnt5a-wildtype or heterozygous mice on either a 129SVbrd or 129×C57B1/6 genetic background were monitored for spontaneous tumor formation. Moribund mice were sacrificed for necropsy, select tissues were harvested for DNA, RNA and protein analysis, and the remaining tissue was fixed in 10% phosphate-buffered formalin and embedded in paraffin wax. Sections were prepared and stained with hematoxylin and eosin and examined microscopically. In some cases, the sections were histochemically stained with B220 antibody or with chloracetate esterase to confirm diagnosis of B cell lymphoma or myeloid leukemia, respectively.

Figure 7:
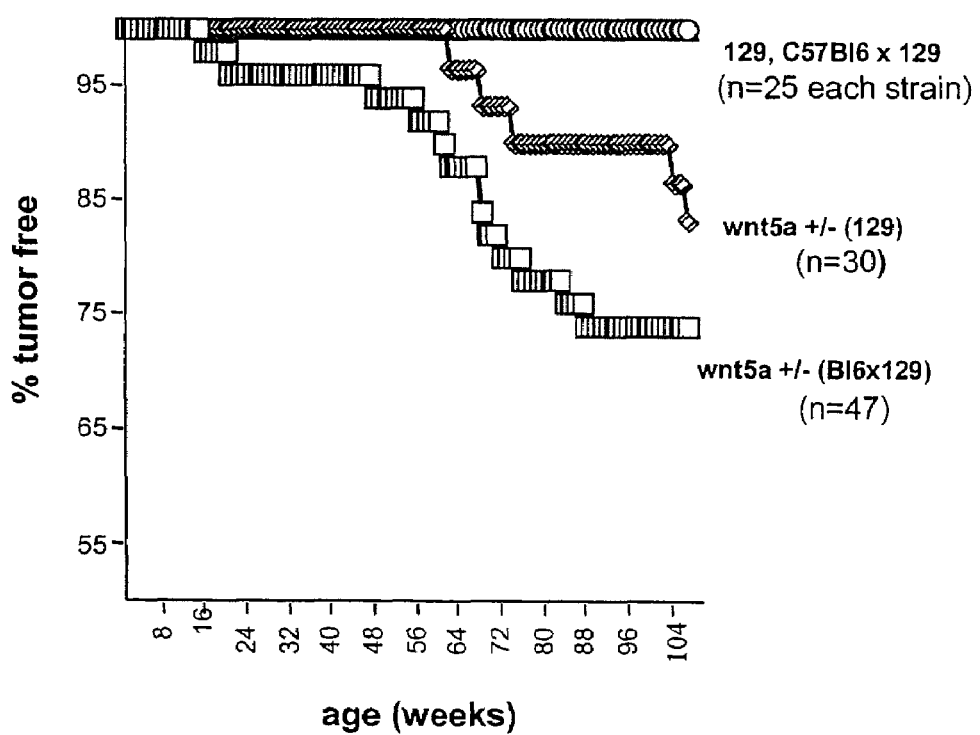
FIG. 7 is a graph depicting the development of tumors (% tumor free animals) over time in various strains of mice. Wild-type 129 and 129×C57B1/6 strain mice (circles) displayed no tumor formation during the time course of the assay. Wnt5a-heterozygous mice on a pure 129-strain background (triangles) or on a mixed, 129×C57B1/6 background (rectangles) presented with spontaneous tumor formation. n=number of mice tested.
Figure 8A:
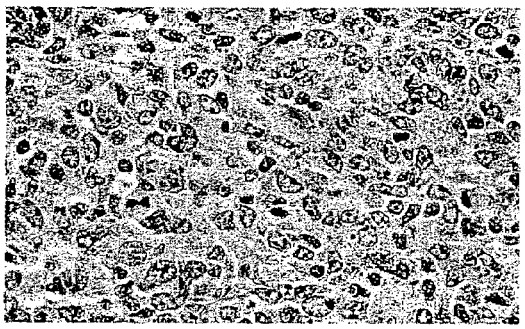
FIGS. 8A-8D are photomicrographs depicting cells in tumors harvested from Wnt5a+/– mice.
Figure 8B:
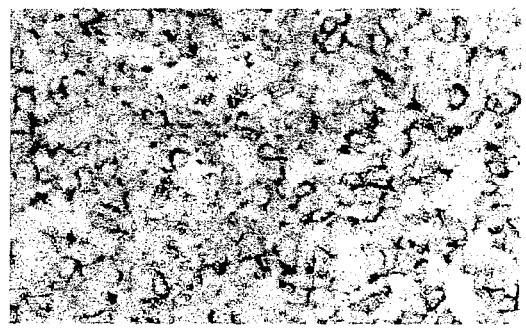
Figure 8C:
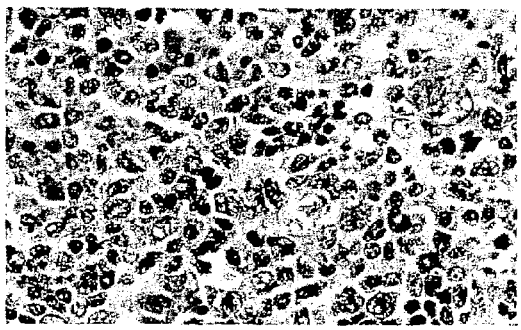
Figure 8D:
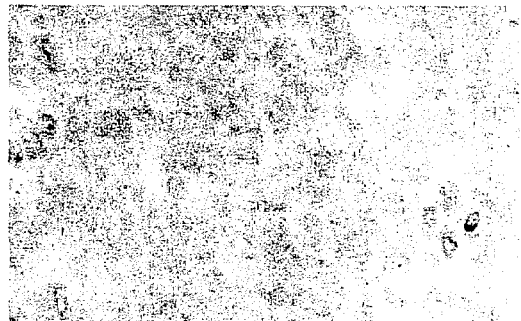

Seventeen percent of inbred 129 Wnt5a-heterozygous mice and twenty-five percent of C57B1/6×129 (mixed background) Wnt5a-heterozygous mice developed spontaneous B cell lymphomas or chronic myeloid leukemias by 24 months of age (FIG. 7). In contrast, age- and strain-matched wild-type control mice remained free of tumors during this time. Affected Wnt5a-heterozygous mice presented with splenomegaly and enlarged liver and lymph glands. Thirty-eight percent of the observed tumors were B cell lymphomas as determined by B220+ staining, with the remainder staining negative for B220+, positive for chloracetate esterase, and classified as myeloid leukemias.

Representative B cell lymphomas were further analyzed to determine if the lymphomas were clonal in origin. Analysis of the clonality of mouse B cell lymphomas was performed as described previously (Rolink et al., 1993). Genomic DNA from representative tumor samples was isolated and used as template for PCR reactions using primer pair: (5' of $D_H$) 5'-acaagcttcaaagcacaatgcctggct-3' (SEQ ID NO:15) and (3' of $J_{H4}$) 5'-gggtctagactctcagccggctccctcaggg-3' (SEQ ID NO:16).

Figure 23:
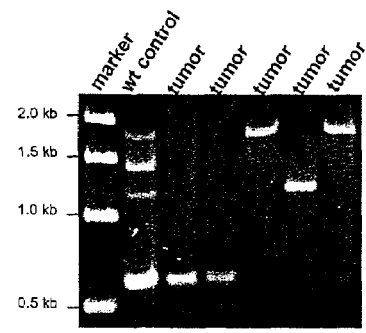
FIG. 23 is a representation of an ethidium bromide-stained agarose gel of PCR results using 5 representative B cell mouse tumors. Wild type spleen (wt) was used as a control.
Figure 24:
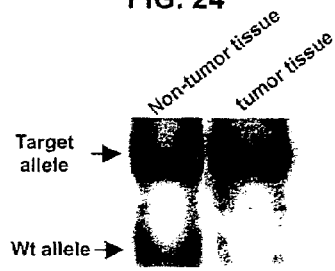
FIG. 24 is a representation of a Southern blot showing the results of analysis of genomic DNA isolated from representative mouse B cell lymphoma demonstrating LOH (loss of heterozygosity) for the wild-type Wnt5a allele.
Figure 22:
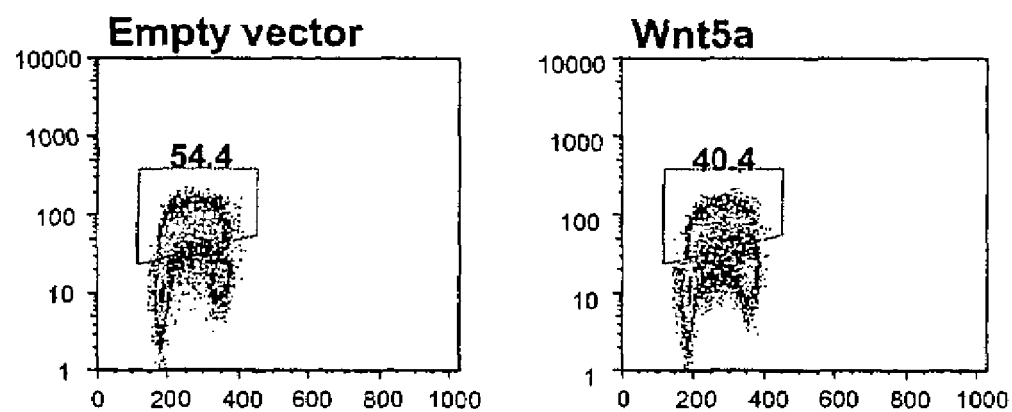
FIG. 22 is a set of four graphs showing the results of cell cycle analysis of asynchronously dividing mouse B cell lines 7C6 (top panels) and 1-8 (bottom panels) transduced with Wnt5a (right panels) or empty vector (left panels), as determined by BrdU uptake (percentage of cells in S phase given).
Figure 22:
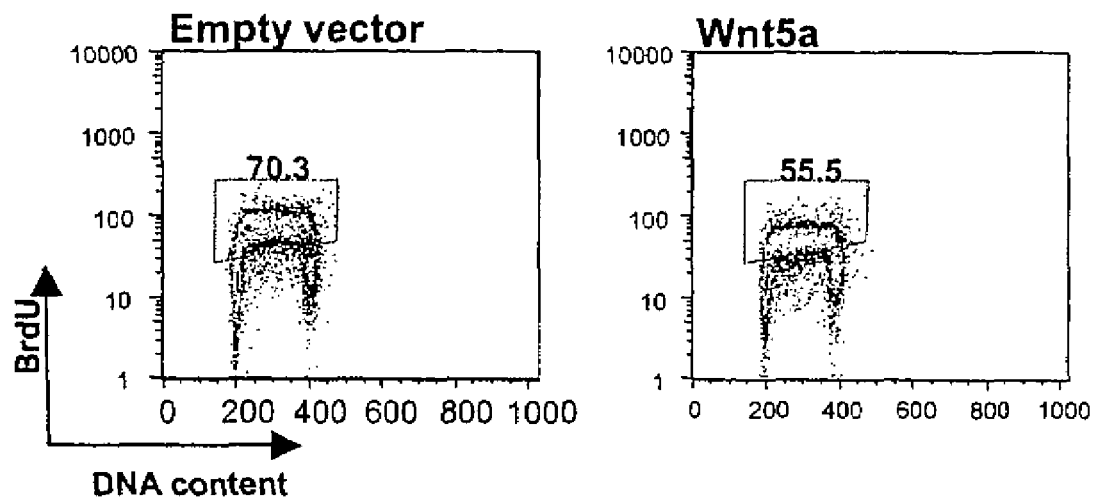

PCR amplification of wildtype mouse spleen yielded a 1.7 Kb $D_H J_{H1}$ fragment, a 1.45 Kb $D_H J_{H2}$ fragment, a 1.1 Kb $D_H J_{H3}$ fragment, and a 0.6 Kb $D_H J_{H4}$ fragment. PCR assays performed using DNA isolated from tumor tissues revealed specific rearrangements of the VDJ region of the immunoglobulin heavy chain locus in each tumor, indicating that the B cell lymphomas were clonal in origin (FIG. 23). Analysis of DNA from a representative B cell lymphomas revealed loss or reduction of the Wnt5a wildtype allele, indicating loss of heterozygosity (LOH) for Wnt5a in the tumor tissue (FIG. 24).

Figure 9:
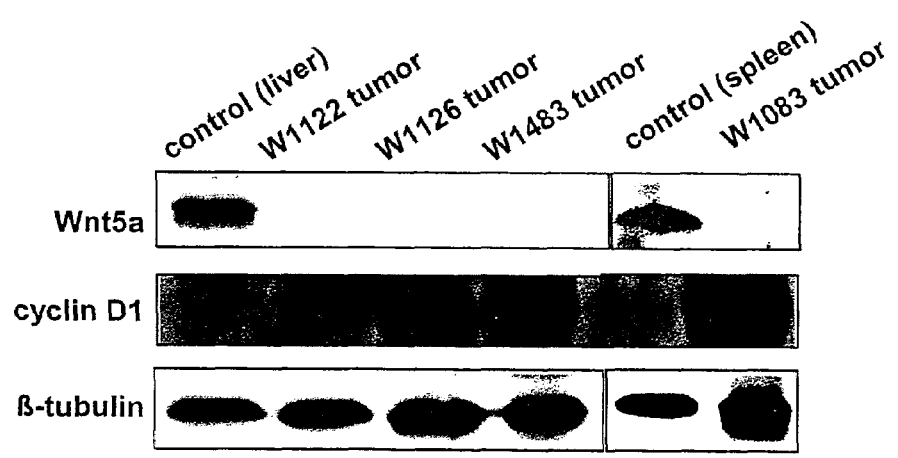
FIG. 9 is a representation of Western blots analyzing Wnt5a (top panel), cyclin D1 (middle panel) and β-tubulin (bottom panel, a positive loading control) expression in normal tissue and various tumor tissues. Loss of Wnt5a expression correlates with tumor formation. Representative tumor samples isolated from liver tumors (W1122, W1126, W1483) or spleen tumors (W1083) and control tissue (Wnt5a+/– non-tumor liver and spleen) were immunoblotted with anti-Wnt5a, anti-cyclin D1, or anti-β-tubulin antibodies.

To confirm loss of Wnt5a function in the tumors, select tumors were isolated from representative mice and analyzed for the presence of Wnt5a protein by Western blot. Wnt5a protein was found to be absent in four of four tumor samples; increased cyclin D1 levels were also observed in these tumor samples (FIG. 9), and two additional samples were determined to have undergone loss of heterozygosity for the wild-type Wnt5a allele in the tumor. The loss of functional Wnt5a in the tumors characterizes Wnt5a as a tumor suppressor in B cell lymphomas and myeloid leukemias.

Example 10

Wnt5a Functions as a Tumor Suppressor in Humans

To determine whether WNT5a can function as a tumor suppressor in human malignancies, total RNA was prepared from normal human peripheral white blood cells, from normal human CD34+ bone marrow cells, and from primary tumor tissues from ten human acute lymphoblastic leukemias (ALL, CD19+ or CD4+) and ten acute myeloid leukemias (AML, CD13+/CD33+).

Human peripheral blood and bone marrow were obtained from subjects diagnosed with either acute lymphoblastic leukemia or acute myeloid leukemia. Healthy, non-cancerous individuals peripheral blood and bone marrow (CD34+) cells were used as controls. White blood cells were isolated by gradient centrifugation of the whole blood over Histopaque-1077 (Sigma). RT-PCR and Southern blot to verify the PCR product specificity were carried out as described above. LOH of Wnt5a in mouse tumor sample was detected by Southern blot as previously described (Yamaguchi et al, 1999 Development 126, 1211-23). For human samples, genomic DNA was isolated from the primary tumor samples and digested with Hind III. A DNA fragment of WNT5a exon 5 coding sequences was generated by PCR using primers 5'-ccagcatcacatcacaacacgg-3' (sense; SEQ ID NO:17) and 5'-atttgggcagcagggaggaaag-3' (antisense; SEQ ID NO:18) and used as probe for the Southern analysis. A human histone H4 gene probe was used as a loading control in these experiments.

Figure 15A:
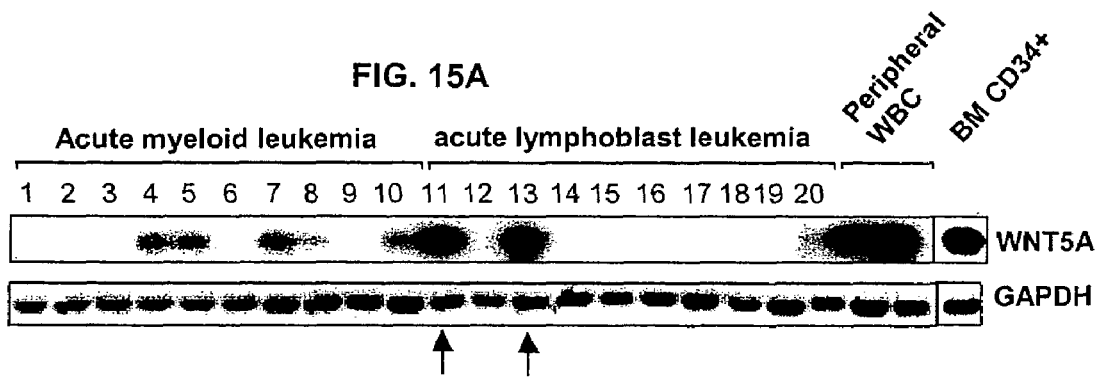
FIG. 15A is a set of representations of autoradiograms depicting Wnt5a (top row) and GAPDH (bottom row, loading control) expression, analyzed by RT-PCR and Southern blot hybridization, in RNA samples extracted from primary tumor tissues in human subjects with acute myeloid leukemia or acute lymphoblast leukemia, and in peripheral white blood cells (WBC) and CD34+ bone marrow (BM) cells from a healthy volunteer.

These samples were analyzed for WNT5a expression by RT-PCR and Southern analysis. WNT5a expression has been reported previously in human B cells and myeloid cells (Van Den Berg et al., *Blood* 92:3189-3202, 1998) and was readily detected in control peripheral white blood cell samples cells as well as in normal human CD34+ bone marrow cells (FIG. 15A). However, eight ALL samples (pre-B cell ALL, CD19+) lacked WNT5a transcripts, whereas two ALL samples (one T cell ALL, CD4+ and CD19−, and one mixed-lineage preB/mycloid cell ALL, CD19+/CD33+) retained WNT5a expression. All of the myeloid leukemia samples displayed either greatly reduced levels or complete absence of WNT5a transcripts. Therefore, loss of WNT5a expression correlates with tumorigenesis in human hematopoietic tissues.

Figure 15B:
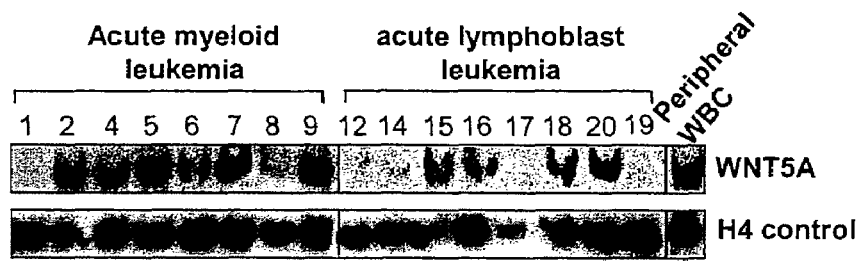
FIG. 15B is a set of representations of autoradiograms depicting the results of analysis by Southern hybridization of the presence of the Wnt5a (top row) and histone H4 (bottom row, control) genes. Loss of Wnt5A is observed in samples 1, 8, 12, 14, 17, and 19.

Eight AML samples and eight B-cell ALL samples were analyzed further for presence of the WNT5a gene. Southern analysis of genomic DNA purified from the tumor tissues was performed using a probe against WNT5a exon 5 coding sequences. Several of the AML samples and half of the B-cell ALL samples displayed either loss or a large reduction in Wnt5a gene dosage (FIG. 15B). Examination of cyclin D1 expression levels in the 8 primary ALL samples lacking WNT5a expression and in all of the AML samples using real time PCR revealed a 4 to 8 fold increase in cyclin D1 expression relative to normal control samples (Table 2).

TABLE 2

Cyclin D1 expression levels of human cancer samples

| Subjects | Leukemia type | Cyclin D1 cycles♣ | GAPDH cycles♣ | Normalized Cyclin D1 cycles♦ | Fold increase in Cyclin D1 expression* |
|---|---|---|---|---|---|
| control | normal | 23.05 | 17.06 | 23.05 | — |
| P1 | AML | 23.47 | 17.13 | 23.37 | −0.6 |
| P2 | AML | 22.41 | 16.78 | 22.78 | 0.5 |
| P3 | AML | 19.83 | 17.45 | 19.38 | 7.3 |
| P4 | AML | 19.37 | 16.61 | 19.89 | 6.3 |
| P5 | AML | 19.38 | 16.80 | 19.67 | 6.7 |
| P6 | AML | 20.46 | 17.22 | 20.26 | 5.5 |
| P7 | AML | 19.14 | 17.08 | 19.11 | 7.8 |
| P8 | AML | 20.21 | 17.17 | 20.08 | 5.9 |
| P9 | AML | 20.01 | 17.03 | 20.04 | 6.0 |
| P10 | AML | 21.25 | 17.18 | 21.10 | 3.8 |
| P12 | PreB-ALL | 21.07 | 16.75 | 21.45 | 3.1 |
| P14 | PreB-ALL | 20.41 | 17.17 | 20.27 | 5.5 |
| P15 | PreB-ALL | 21.14 | 17.27 | 20.88 | 4.3 |
| P16 | PreB-ALL | 19.82 | 17.2 | 19.65 | 6.7 |
| P17 | PreB-ALL | 21.25 | 16.95 | 21.38 | 3.3 |
| P18 | preB-ALL | 21.05 | 16.91 | 21.23 | 3.6 |
| P19 | PreB-ALL | 19.71 | 16.64 | 20.20 | 5.6 |
| P20 | PreB-ALL | 22.07 | 17.46 | 21.56 | 2.9 |

♣The threshold cycle number for each sample was calculated using the Applied Biosystems ABI prism 7700 sequence detection system software at a fluorescence threshold (Rn) of 0.011.
♦Threshold cycle numbers of the tumor samples were normalized for GAPDH
*The increase in cyclin D1 expression was calculated by multiplying by two the difference between the normalized threshold cycle numbers of the tumor sample and of control.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed:

1. A method of determining whether a mammal has acute lymphoblastic leukemias (ALL) or acute myeloid leukemias (AML), the method comprising: providing a biological sample comprising a test cell from the mammal, wherein the test cell is a lymphoid cell or a myeloid cell; and determining the level of Wnt5a mRNA within the test cell, wherein a significantly reduced level of Wnt5a mRNA in the test cell, relative to that in a non-cancerous control lymphoid or myeloid cell of the same type as the test cell, indicates that the mammal has ALL or AML.

2. The method of claim 1, wherein the mammal is a human patient.

3. The method of claim 1, wherein the acute leukemia is acute myeloid leukemia (AML).

4. The method of claim 1, wherein the acute leukemia is acute lymphoblast leukemia (ALL).

5. The method of claim 1, wherein both the test cell and the control cell are B cells, T cells, eosinophils, basophils, erythrocytes, neutrophils, granulocytes, or monocytes.

6. The method of claim 1, further comprising culturing one or both of the test cell and the control cell before determining the level of Wnt5a mRNA.

7. The method of claim 1, wherein determining the level of Wnt5a mRNA comprises exposing mRNA isolated from the test cell to a Wnt5a-specific nucleic acid primer or probe.

8. The method of claim 1, wherein both the test cell and the control cell are human cells.

9. The method of claim 1, wherein both the test cell and the control cell are lymphoid cells, and a reduced level of Wnt5a mRNA in the test cell, relative to that in the control cell, indicates that the mammals has ALL.

10. The method of claim 1, wherein both the test cell and the control cell are myeloid cells, and a reduced level of Wnt5a mRNA in the test cell, relative to that in the control cell, indicates that the mammal has AML.

* * * * *

UNITED STATES PATENT AND TRADEMARK OFFICE
CERTIFICATE OF CORRECTION

| | |
|---|---|
| PATENT NO. | : 7,723,055 B2 |
| APPLICATION NO. | : 11/874703 |
| DATED | : May 25, 2010 |
| INVENTOR(S) | : Stephen N. Jones, Huiling Liang and German Pihan |

It is certified that error appears in the above-identified patent and that said Letters Patent is hereby corrected as shown below:

At Column 42, line 38 (approx.), in Claim 9, delete "mammals" and insert -- mammal --.

Signed and Sealed this

Thirty-first Day of August, 2010

David J. Kappos
*Director of the United States Patent and Trademark Office*

SEQUENCE LISTING

```
<160> NUMBER OF SEQ ID NOS: 18

<210> SEQ ID NO 1
<211> LENGTH: 25
<212> TYPE: DNA
<213> ORGANISM: Artificial Sequence
<220> FEATURE:
<223> OTHER INFORMATION: PCR primer

<400> SEQUENCE: 1
ctacgagagt gctcgcatcc tcatg                                           25

<210> SEQ ID NO 2
<211> LENGTH: 21
<212> TYPE: DNA
<213> ORGANISM: Artificial Sequence
<220> FEATURE:
<223> OTHER INFORMATION: PCR primer

<400> SEQUENCE: 2
cattgcgcac gcagtagtca g                                               21

<210> SEQ ID NO 3
<211> LENGTH: 18
<212> TYPE: DNA
<213> ORGANISM: Artificial Sequence
<220> FEATURE:
<223> OTHER INFORMATION: PCR primer

<400> SEQUENCE: 3
```
tcgggactgg ttgtgggg                                              18

<210> SEQ ID NO 4
<211> LENGTH: 18
<212> TYPE: DNA
<213> ORGANISM: Artificial Sequence
<220> FEATURE:
<223> OTHER INFORMATION: PCR primer

<400> SEQUENCE: 4
agctcgcagc cgtccatc                                              18

<210> SEQ ID NO 5
<211> LENGTH: 20
<212> TYPE: DNA
<213> ORGANISM: Artificial Sequence
<220> FEATURE:
<223> OTHER INFORMATION: PCR primer

<400> SEQUENCE: 5
cagcctcaag atcatcagca                                            20

<210> SEQ ID NO 6
<211> LENGTH: 20
<212> TYPE: DNA
<213> ORGANISM: Artificial Sequence
<220> FEATURE:
<223> OTHER INFORMATION: PCR primer

<400> SEQUENCE: 6
tgagcttgac aaagtggtcg                                            20

<210> SEQ ID NO 7
<211> LENGTH: 20
<212> TYPE: DNA
<213> ORGANISM: Artificial Sequence
<220> FEATURE:
<223> OTHER INFORMATION: PCR primer

<400> SEQUENCE: 7
caccatggag aaggccgggg                                            20

<210> SEQ ID NO 8
<211> LENGTH: 20
<212> TYPE: DNA
<213> ORGANISM: Artificial Sequence
<220> FEATURE:
<223> OTHER INFORMATION: PCR primer

<400> SEQUENCE: 8
gacggacaca ttgggggtag                                            20

<210> SEQ ID NO 9
<211> LENGTH: 20
<212> TYPE: DNA
<213> ORGANISM: Artificial Sequence
<220> FEATURE:
<223> OTHER INFORMATION: PCR primer

<400> SEQUENCE: 9
gcgtaccctg acaccaatct                                            20

<210> SEQ ID NO 10
<211> LENGTH: 20
<212> TYPE: DNA

```
<213> ORGANISM: Artificial Sequence
<220> FEATURE:
<223> OTHER INFORMATION: PCR primer

<400> SEQUENCE: 10
cacaacttct cggcagtcaa                                                      20

<210> SEQ ID NO 11
<211> LENGTH: 20
<212> TYPE: DNA
<213> ORGANISM: Artificial Sequence
<220> FEATURE:
<223> OTHER INFORMATION: PCR primer

<400> SEQUENCE: 11
tgcgacgagg aagagaattt                                                      20

<210> SEQ ID NO 12
<211> LENGTH: 20
<212> TYPE: DNA
<213> ORGANISM: Artificial Sequence
<220> FEATURE:
<223> OTHER INFORMATION: PCR primer

<400> SEQUENCE: 12
aaccgctcca catacagtcc                                                      20

<210> SEQ ID NO 13
<211> LENGTH: 20
<212> TYPE: DNA
<213> ORGANISM: Artificial Sequence
<220> FEATURE:
<223> OTHER INFORMATION: PCR primer

<400> SEQUENCE: 13
cccgcacgat ttcattgaac                                                      20

<210> SEQ ID NO 14
<211> LENGTH: 22
<212> TYPE: DNA
<213> ORGANISM: Artificial Sequence
<220> FEATURE:
<223> OTHER INFORMATION: PCR primer

<400> SEQUENCE: 14
gcggattgga aatgaacttc ac                                                   22

<210> SEQ ID NO 15
<211> LENGTH: 27
<212> TYPE: DNA
<213> ORGANISM: Artificial Sequence
<220> FEATURE:
<223> OTHER INFORMATION: PCR primer

<400> SEQUENCE: 15
acaagcttca aagcacaatg cctggct                                              27

<210> SEQ ID NO 16
<211> LENGTH: 31
<212> TYPE: DNA
<213> ORGANISM: Artificial Sequence
<220> FEATURE:
<223> OTHER INFORMATION: PCR primer

<400> SEQUENCE: 16
gggtctagac tctcagccgg ctccctcagg g                                         31
```

```
<210> SEQ ID NO 17
<211> LENGTH: 22
<212> TYPE: DNA
<213> ORGANISM: Artificial Sequence
<220> FEATURE:
<223> OTHER INFORMATION: PCR primer

<400> SEQUENCE: 17
ccagcatcac atcacaacac gg                                        22

<210> SEQ ID NO 18
<211> LENGTH: 22
<212> TYPE: DNA
<213> ORGANISM: Artificial Sequence
<220> FEATURE:
<223> OTHER INFORMATION: PCR primer

<400> SEQUENCE: 18
atttgggcag cagggaggaa ag                                        22
```